US010906845B2

(12) United States Patent
West et al.

(10) Patent No.: US 10,906,845 B2
(45) Date of Patent: Feb. 2, 2021

(54) MICROBIAL INOCULANTS, FERTILISER COMPOSITIONS, GROWTH MEDIUMS AND METHODS FOR ENHANCING PLANT GROWTH

(71) Applicant: Sustainable Organic Solutions Pty Ltd, Middle Park (AU)

(72) Inventors: Stephen West, Middle Park (AU); Evgeny Sagulenko, Middle Park (AU); Nikolai Kinaev, Middle Park (AU)

(73) Assignee: Sustainable Organic Solutions Pty Ltd, Middle Park (AU)

( * ) Notice: Subject to any disclaimer, the term of this patent is extended or adjusted under 35 U.S.C. 154(b) by 0 days.

(21) Appl. No.: 15/579,659

(22) PCT Filed: Jun. 3, 2016

(86) PCT No.: PCT/AU2016/050453
§ 371 (c)(1),
(2) Date: Dec. 5, 2017

(87) PCT Pub. No.: WO2016/191828
PCT Pub. Date: Dec. 8, 2016

(65) Prior Publication Data
US 2018/0170819 A1 Jun. 21, 2018

(30) Foreign Application Priority Data
Jun. 5, 2015 (AU) .................................. 2015902251

(51) Int. Cl.
*C05F 11/08* (2006.01)
*C12R 1/01* (2006.01)
(Continued)

(52) U.S. Cl.
CPC ................ *C05F 11/08* (2013.01); *A01H 3/00* (2013.01); *A01N 63/00* (2013.01); *C05B 15/00* (2013.01);
(Continued)

(58) Field of Classification Search
CPC .... C05F 11/08; C05F 9/04; C05F 3/00; C05B 15/00; A01N 63/00; A01H 3/00;
(Continued)

(56) References Cited

U.S. PATENT DOCUMENTS 9,687,000 B2   6/2017   Bullis et al.

FOREIGN PATENT DOCUMENTS

| JP | 2005110526 | 4/2005 |
| JP | 2015502751 | 12/2017 |

(Continued)

OTHER PUBLICATIONS

Kifle, Medhin Hadish. Evaluation of Diazotrophic Bacteria as Biofertilizers. Diss. University of KwaZulu-Natal, Pietermaritzburg, 2013.*

(Continued)

*Primary Examiner* — Jennifer A Smith
(74) *Attorney, Agent, or Firm* — Steptoe & Johnson LLP

(57) ABSTRACT

The present invention relates to microbial inoculants, fertiliser compositions, growth mediums and methods for enhancing plant growth. In one aspect, the invention relates to a method of increasing plant growth, plant productivity, seed germination or soil quality for a dicotyledonous plant or a monocotyledonous plant, the method comprising the step of: applying to the plant a treatment agent comprising at least one plant-beneficial *Burkholderia*-like species.

16 Claims, 3 Drawing Sheets

Specification includes a Sequence Listing.

(51) Int. Cl.
   *A01N 63/00* (2020.01)
   *A01H 3/00* (2006.01)
   *C05B 15/00* (2006.01)
   *C05F 3/00* (2006.01)
   *C05F 9/04* (2006.01)

(52) U.S. Cl.
   CPC .................. *C05F 3/00* (2013.01); *C05F 9/04* (2013.01); *C12R 1/01* (2013.01); *Y02A 40/20* (2018.01); *Y02P 20/145* (2015.11)

(58) Field of Classification Search
   CPC ....... C12R 1/01; Y02A 40/205; Y02A 40/216; Y02P 20/145
   See application file for complete search history.

(56) References Cited

FOREIGN PATENT DOCUMENTS

| | | |
|---|---|---|
| WO | 2013/063658 | 5/2013 |
| WO | 2013/090628 | 6/2013 |
| WO | 2013/190082 | 12/2013 |
| WO | 2014/210372 | 12/2014 |

OTHER PUBLICATIONS

Alves, G.C. et al., 'Plant growth promotion by four species of the genus *Burkhoderia*', Plant and Soil, Feb. 2016, vol. 399, pp. 373-387.
Anandham, R. et al., 'Potential plant growth promoting traits and bioacidulation of rock phosphate by thiosulfate oxidizing bacteria isolated from crop plants', Journal of Basic Microbiology, 2008, vol. 48, pp. 439-447.
Angus AA, Agapakis CM, Fong S, Yerrapragada S, Estrada-de los Santos P, Yang P, Song N, Kano S, Caballero-Mellado J, de Faria SM, Dakora FD, Weinstock G,Hirsch AM. Plant-associated symbiotic *Burkholderia* species lack hallmark strategies required in mammalian pathogenesis. PLoS One. Jan. 8, 2014;9(1):e83779. doi: 10.1371/journal.pone.0083779. eCollection 2014. PubMed PMID: 24416172;PubMed Central PMCID: PMC3885511.
Bhattacharyya PN, Jha DK. Plant growth-promoting rhizobacteria (PGPR): emergence in agriculture. World J Microbiol Biotechnol. Apr. 2012;28(4):1327-50. doi: 10.1007/s11274-011-0979-9. Epub Dec. 24, 2011. Review. PubMed PMID: 22805914.
Caballero-Mellado, J. et al., 'The tomato rhizosphere, an environment rich in nitrogen-fixing *Burkholderia* species with capabilities of interest for agriculture and bioremediation', Applied and Environmental Microbiology, 2007, vol. 73, pp. 5308-5319.
Carroll P. Vance, Claudia Uhde-Stone, Deborah L. Allan. Phosphorus acquisition and use: critical adaptations by plants for securing a nonrenewable resource. New Phytologist. (2003) DOI: 10.1046/j.1469-8137.2003.00695.x.
Choudhury AT, Kennedy IR, Ahmed MF, Kecskés ML. Phosphorus fertilization for rice and control of environmental pollution problems. Pak J Biol Sci. Jul. 1, 2007;10(13):2098-105. Review. PubMed PMID: 19070168.
Fudali SL, Wang C, Williamson VM. Ethylene signaling pathway modulates attractiveness of host roots to the root-knot hematode Meloidogyne hapla. Mol Plant Microbe Interact. Jan. 2013;26(1):75-86. doi: 10.1094/MPMI-05-12-0107-R. PubMed PMID: 22712507.
GenBank Accession No. AY586520 Apr. 28, 2004.
GenBank Accession No. EF139182 May 5, 2015.
GenBank Accession No. EF139183 May 5, 2015.
GenBank Accession No. EF139187 May 5, 2015.
GenBank Accession No. EF397576 Aug. 27, 2014.
GenBank Accession No. FR872419 Apr. 10, 2013.
GenBank Accession No. HM467915 May 31, 2012.
GenBank Accession No. KC608183 Sep. 22, 2014.
Gonin, M. et al., 'Rhizosphere bacteria of *Costularia* spp. from ultramafic soils in New Caledonia: diversity, tolerance to extreme edaphic conditions, and role in plant growth and mineral nutrition', Canadian Journal of Microbiology, 2013, vol. 59, pp. 164-174.
Guo, J. et al., 'Effects of inoculation of a plant growth promoting rhizobacterium *Burkholderia* sp. D54 on plant growth and metal uptake by a hyperaccumulator Sedum alfredii Hance grown on multiple metal contaminated soil', World Journal of Microbiology and Biotechnology, 2011, vol. 27, pp. 2835-2844, DOI 10.1007/s11274-011-0762-y.
Mattos, K.A. et al., 'Endophytic colonization of rice (*Oryza sativa* L.) by the diazotrophic bacterium Burkholderia kururiensis and its ability to enhance plant growth', Anais da Academia Brasileira de Ciências, 2008, vol. 80, pp. 177-493.
Miransari M. Soil microbes and plant fertilization. Appl Microbiol Biotechnol. Dec. 2011;92(5):875-85. doi: 10.1007/s00253-011-3521-y. Epub Oct. 12, 2011. Review. PubMed PMID: 21989562.
Mulvaney RL, Khan SA, Ellsworth TR. Synthetic nitrogen fertilizers deplete soil nitrogen: a global dilemma for sustainable cereal production. J Environ Qual. Oct. 29, 2009;38(6):2295-314. doi: 10.2134/jeq2008.0527. Print Nov.-Dec. 2009. Review. PubMed PMID: 19875786.
Naveed, M. et al., 'Drought stress amelioration in wheat through inoculation with Burkholderia phytofirmans strain PsJN', Plant Growth Regulation, 2014, vol. 73, pp. 121-131.
Naik PR, Raman G, Narayanan KB, Sakthivel N. Assessment of genetic and functional diversity of phosphate solubilizing fluorescent pseudomonads isolated from rhizospheric soil. BMC Microbiol. Dec. 20, 2008;8:230. doi:10.1186/1471-2180-8-230. PubMed PMID: 19099598; PubMed Central PMCID: PMC2625360.
NCBI Reference Sequence NR_102845 Feb. 3, 2015.
Noppadol Prasertsincharoen et al. Effects of colonization of the roots of domestic rice (*Oryza sativa* L cv. Amaroo) by Burkholderia psudomallei. Applied and Environmental Microbiology. 2015, vol. 81, pp. 4368-4375.
Paungfoo-Lonhienne, C. et al., 'A new species of *Burkholderia* isolated from sugarcane roots promotes plant growth', Microbial Biotechnology, 2014, vol. 7, pp. 142-154.
Paungfoo-Lonhienne, C. et al., 'Crosstalk Between Sugarcane and a Plant-Growth Promoting *Burkholderia* Species', Scientific Reports, 2016, vol. 6, Article 37389 (Published online Nov. 21, 2016).
Saha M, Sarkar S, Sarkar B, Sharma BK, Bhattacharjee S, Tribedi P. Microbial siderophores and their potential applications: a review. Environ Sci Pollut Res Int. Mar. 12, 2015. [Epub ahead of print] PubMed PMID: 25758420.
Sharma SB, Sayyed RZ, Tribedi MH, Gobi TA. Phosphate solubilizing microbes: sustainable approach for managing phosphorus deficiency in agricultural soils. Springerplus. Oct. 31, 2013;2:587. doi: 10.1186/2193-1801-2-587. eCollection 2013. Review. PubMed PMID: 25674415; PubMed Central PMCID: PMC4320215.
Suárez-Moreno ZR, Caballero-Mellado J, Coutinho BG, Mendonça-Previato L, James EK, Venturi V. Common features of environmental and potentially beneficial plant-associated Burkholderia. Microb Ecol. Feb. 2012;63(2):249-66. doi: 10.1007/s00248-011-9929-1. Epub Aug. 18, 2011. Review. PubMed PMID: 21850446.
Xincheng Zhang et al. Colonization and Modulation of Host Growth and Metal Uptake by Endophytic Bacteria of Sedum Alfredii. International Journal of Phytoremediation, 2013, vol. 15, pp. 51-64.
Young CC, Rekha PD, Lai WA, Awrun AB. Encapsulation of plant growth-promoting bacteria in alginate beads enriched with humic acid. Biotechnol Bioeng. Sep. 5, 2006;95(1):76-83.
International Preliminary Report on Patentability which issued in respect of PCT/AU2016/050453, dated May 9, 2017.
International Opinion which issued in respect of PCT/AU2016/050453, dated Sep. 12, 2016.
International Search Report which issued in respect of PCT/AU2016/050453, dated Sep. 12, 2016.
Extended European Search Report which issued in respect of corresponding EP Application No. 16802258.0, dated Jan. 28, 2019.
Office action mailed mailed in Japanese Patent Application 2017-563236 dated Aug. 4, 2020, and its translation.

\* cited by examiner

SEQUENCE LISTING

<160> NUMBER OF SEQ ID NOS: 5

<210> SEQ ID NO 1
<211> LENGTH: 1382

```
<212> TYPE: DNA
<213> ORGANISM: Unknown
<220> FEATURE:
<223> OTHER INFORMATION: Bacterium SOS1
<220> FEATURE:
<221> NAME/KEY: misc_feature
<222> LOCATION: (1188)..(1188)
<223> OTHER INFORMATION: n is a, c, g, or t

<400> SEQUENCE: 1
aagtcggacg gcagcgcggg ggcaaccctg gcggcgagtg gcgaacgggt gagtaataca      60
tcggaacgtg tcctggagtg gggggatagcc ggcgaaagcc ggattaatac cgatacgctc    120
tgtggaggaa agcgggggat cttcggacct cgcgctcaag gggcggccga tgcagatta     180 gctagttggt ggggtaaagg cctaccaagg cgacgatctg tagctggtct gagaggacga    240
ccagccacac tgggactgag acacggccca gactcctacg ggaggcagca gtggggaatt    300
ttggacaatg ggggcaaccc tgatccagca atgccgcgtg tgtgaagaag ccttcgggt     360 tgtaaagcac ttttgtccgg aaagaaaacc gcttctctaa tacaggggcg ggatgacggt    420
accggaagaa taagcaccgg ctaactacgt gccagcagcc gcggtaatac gtagggtgca    480
agcgttaatc ggaattactg ggcgtaaagc gtgcgcaggc ggttcgctaa gaccgatgtg    540
aaatccccgg gcttaacctg gaactgcat tggtgactgg cgggctagag tatggcagag     600
gggggtagaa ttccacgtgt agcagtgaaa tgcgtagaga tgtggaggaa taccgatggc    660
gaaggcagcc ccctgggcca atactgacgc tcatgcacga aagcgtgggg agcaaacagg    720
attagatacc ctggtagtcc acgccctaaa cgatgtcaac tagttgtcgg gtcttcattg    780
acttggtaac gaagctaacg cgtgaagttg accgcctggg gagtacggtc gcaagattaa    840
aactcaaagg aattgacggg acccgcaca agcgtggatg atgtggatta attcgatgca     900
acgcgaaaaa ccttacctac ccttgacatg tacggaacct tgctgagagg tgagggtgcc    960
cgaaagggag ccgtaacaca ggtgctgcat ggctgtcgtc agctcgtgtc gtgagatgtt   1020
gggttaagtc ccgcaacgag cgcaacccctt gtccctagtt cgtacgcaag agcactctag  1080
ggagactgcc ggtgacaaac cggaggaagg tggggatgac gtcaagtcct catggccctt   1140
atgggtaggg cttcacacgt catacaatgg tcggaacaga ggttgcnaa gccgcgaggt    1200 ggagccaatc ccagaaaacc gatcgtagtc cggatcgcag tctgcaactc gactgcgtga   1260
agctggaatc gctagtaatc gcggatcagc atgccgcggt gaatacgttc ccgggtcttg   1320
tacacaccgc ccgtcacacc atgggagtgg gttttaccag aagtggctag tctaaccgca   1380
ag                                                                  1382

<210> SEQ ID NO 2
<211> LENGTH: 1440
<212> TYPE: DNA
<213> ORGANISM: Unknown
<220> FEATURE:
<223> OTHER INFORMATION: Bacterium SOS2

<400> SEQUENCE: 2
gctggcggca tgctttacac atgcaagtcg aacggcagca cggggggcaac cctggtggcg      60 agtggcgaac gggtgagtaa tacatcggaa cgtgtcctgg agtgggggat agcccggcga   120
aagccggatt aataccgcat acgctcggga gaggaaagcg ggggaccttc gggcctcgcg   180
ctcaaggggc ggccgatggc ggattagcta gttggtgggg taaaggccta ccaaggcgac   240
gatccgtagc tggtctgaga ggacgaccag ccacactggg actgagacac ggcccagact   300
```

```
cctacgggag gcagcagtgg ggaattttgg acaatggggg caaccctgat ccagcaatgc      360
cgcgtgtgcg aagaaggcct tcggttgta aagcactttt gtccggaaag aaatcctgcc       420
tgataatacc gggcgggat  gacggtaccg aagaataag  caccggctaa ctacgtgcca      480
gcagccgcgg taatacgtag ggtgcgagcg ttaatcggaa ttactgggcg taaagcgtgc      540
gcaggcggtt cgctaagacc gatgtgaaat ccccgggctt aacctgggaa ctgcattggt      600
gactggcggg ctagagtatg gcagaggggg gtagaattcc acgtgtagca gtgaaatgcg      660
tagagatgtg gaggaatacc gatggcgaag gcagccccct gggccaatac tgacgctcat      720
gcacgaaagc gtgggagca  aacaggatta gatacctgg  tagtccacgc cctaaacgat      780
gtcaactagt tgttggggat tcatttcctt agtaacgaag ctaacgcgtg aagttgaccg      840
cctggggagt acggtcgcaa gattaaaact caaaggaatt gacggggacc cgcacaagcg      900
gtggatgatg tggattaatt cgatgcaacg cgaaaaacct tacctaccct tgacatggac      960
ggaatcccgc tgagaggtgg gagtgctcga aagagaaccg tcgcacaggt gctgcatggc     1020
tgtcgtcagc tcgtgtcgtg agatgttggg ttaagtcccg caacgagcgc aacccttgtc     1080
cttagttgct acgcaagagc actctaagga gactgccggt gacaaaccgg aggaaggtgg     1140
ggatgacgtc aagtcctcat ggcccttatg ggtagggctt cacacgtcat acaatggtcg     1200
gaacagaggg tcgccaaccc gcgaggggga gccaatccca gaaaaccgat cgtagtccgg     1260
attgcactct gcaactcgag tgcatgaagc tggaatcgct agtaatcgcg gatcagcatg     1320
ccgcggtgaa tacgttcccg ggtcttgtac acaccgcccg tcacaccatg ggagtgggtt     1380
ttaccagaag tggctagtct aaccgcaagg aggacggtca ccacggtagg attcatgact     1440

<210> SEQ ID NO 3
<211> LENGTH: 1288
<212> TYPE: DNA
<213> ORGANISM: Unknown
<220> FEATURE:
<223> OTHER INFORMATION: Bacterium SOS3

<400> SEQUENCE: 3
agtgggggat agcccggcga aagccggatt aataccgcat acgatctgag gatgaaagcg       60
ggggaccgca aggcctcgcg ctcaaggagc ggccgatggc ggattagcta gttggtgggg      120
taaaggccca ccaaggcgac gatccgtagc tggtctgaga ggacgaccag ccacactggg      180
actgagacac ggcccagact cctacgggag gcagcagtgg ggaattttgg acaatggggg      240
caaccctgat ccagcaatgc cgcgtgtgtg aagaaggcct tcgggttgta aagcactttt      300
gtccggaaag aaaacttcgt ccctaatatg gatggaggat gacggtaccg aagaataag       360
caccggctaa ctacgtgcca gcagccgcgg taatacgtag ggtgcgagcg ttaatcggaa      420
ttactgggcg taaagcgtgc gcaggcggtg atgtaagacc gatgtgaaat ccccgggctt      480
aacctgggaa ctgcattggt gactgcattg ctggagtatg gcagaggggg gtggaattcc      540
acgtgtagca gtgaaatgcg tagagatgtg gaggaacacc gatggcgaag gcagccccct      600
gggccaatac tgacgctcat gcacgaaagc gtgggagca  aacaggatta gatacctgg      660
tagtccacgc cctaaacgat gtcaactggt tgtcggcct  tcattggctt ggtaacgtag      720
ctaacgcgtg aagttgaccg cctggggagt acggtcgcaa gattaaaact caaaggaatt      780
gacggggacc cgcacaagcg gtggatgatg tggattaatt cgatgcaacg cgaaaaacct      840
tacctaccct tgacatggac ggaacctcga tgagagttga gggtgccga aagggagccg      900
tcacacaggt gctgcatggc tgtcgtcagc tcgtgtcgtg agatgttggg ttaagtcccg      960
```

```
caacgagcgc aacccttgtc cctggttgct acgcaagagc actccaggga gactgccggt    1020
gacaaaccgg aggaaggtgg ggatgacgtc aagtcctcat ggcccttatg ggtagggctt    1080
cacacgtcat acaatggtcg gaacagaggg ttgccaagcc gcgaggtgga gccaatccca    1140
gaaaaccgat cgtagtccgg atcgcagtct gcaactcgac tgcgtgaagc tggaatcgct    1200
agtaatcgcg gatcagcatg ccgcggtgaa tacgttcccg ggtcttgtac acaccgcccg    1260
tcacaccatg ggagtgggtt ttaccaga                                       1288

<210> SEQ ID NO 4
<211> LENGTH: 18
<212> TYPE: DNA
<213> ORGANISM: Burkholderia sp.

<400> SEQUENCE: 4
gttggcaacc ctctgttc                                                  18

<210> SEQ ID NO 5
<211> LENGTH: 20
<212> TYPE: DNA
<213> ORGANISM: Burkholderia sp.

<400> SEQUENCE: 5
aaactyaaak gaattgacgg                                                20
```

MICROBIAL INOCULANTS, FERTILISER COMPOSITIONS, GROWTH MEDIUMS AND METHODS FOR ENHANCING PLANT GROWTH

CLAIM PRIORITY

This application claims the benefit under 35 USC 371 to International Application No. PCT/AU2016/050453, filed Jun. 3, 2016, which claims priority to AU Patent Application No. 2015902251, filed Jun. 5, 2015, each of which is incorporated by reference in its entirety.

TECHNICAL FIELD

The present invention generally relates to microbial inoculants, fertiliser compositions and growth mediums comprising microorganisms described herein. The disclosure also relates to methods of promoting plant growth and seed germination.

BACKGROUND ART

The use of fertilizers to enhance plant and crop production and overcome poor soil quality is widespread and well known. Commercially available fertilizers typically comprise inorganic chemical fertilizers. Such fertilizers can be potentially hazardous to use and are often associated with environmentally damaging consequences, such as nitrate contamination in run off and ground water. Therefore, long-term use of chemical fertilisers has a negative impact on environmental sustainability and there is at least a need for limiting and preferably avoiding the use of chemical fertilizers.

According to the Food Agriculture Organization (FAO) statistics (ref. 1), the value generated worldwide by crops of Solanaceae (e.g. tomato, potato), Poaceae (e.g. rice, wheat, and maize), in 2012 was estimated to be more than US$200 bn. The downside of this industry is that in order to maintain high yield of production, producers add an excess of inorganic fertilizers which is costly, and which leads to soil and yield decline and offsite pollution. Next-generation agriculture should to be based on ecological principles and generate high yields at low economic and environmental costs. Such enabling technologies and delivery methodologies are yet to be developed.

Nitrogen and phosphorus are among the most important elements required for plant growth and their extensive use in modern agriculture is economically and environmentally costly. Acquisition of nitrogen from the air represents a formidable advantage in agriculture, as it is for legumes. Plants require high amount of nitrogen but are not able to directly fix it from the air. To promote plant growth the agricultural industry applies every year millions of tons of inorganic nitrogen fertilisers to compensate for the low rate of decomposition of organic nitrogen by crops. However, the economic and environmental costs of the heavy use of chemical nitrogen fertilizers are a global concern, as it has a strong negative impact on the environment (ref. 5).

Phosphorus is also a major limiting factor for plant growth as its soluble inorganic form is naturally largely unavailable for root uptake. It has been estimated that in the natural environment, only 0.1% of the total phosphorus exists in a soluble form available for plant uptake (ref. 6). For this reason, phosphate fertilizers are widely used in agriculture to increase crop yield. However, it has been estimated that the world's known reserves of high quality rock phosphorus may be depleted by 2050, which will make it highly expensive for agricultural use (ref. 7). Moreover, its excessive application displays adverse environmental impacts on terrestrial, freshwater and marine resources. The efficiency of the applied fertilizers rarely exceeds 30%, and the repeated and injudicious applications of phosphate fertilizers leads to the loss of soil fertility (ref. 8). All these factors have pressed to the search for environmental compatible and economically feasible alternative strategies.

An alternative approach to feed plants is to apply organic fertilizers (e. g. livestock manure and compost). Organic fertilizers represent an environmentally friendly way of delivery of nutrients to plants. Manure is a waste product of living organisms. Compared to inorganic fertilizers organic fertilizers do not cause pollution of ground water and stripping of soil nutrients and they also normally do not burn plant roots. Organic fertilizers improve the health and vitality of the soil structure. Soils with lots of organic material hold more moisture and nutrients, promoting growth of soil organisms and plant root development. The problem with application of organic fertilizers is the slow release of nutrients from them, whereas mineral fertilizers are usually water-soluble and thus immediately available to plants.

Fertilizer compositions and plant growth mediums comprising microorganisms (also known in the art as "biofertilizers") are increasingly considered as alternatives to conventional chemical fertilizers. A promising avenue in future agricultural practice is application of biofertilizers based on the Plant Growth Promoting Rhizobacteria (PGPR), to enhance plant growth and vigor (refs. 2 and 3). Globally, agro-industries are starting embracing PGPR technology with significant investment by a number of companies including Syngenta and Monsanto (ref. 4). However, the efficacy of PGPR differs widely, with no benefits to considerable benefits being reported, and reasons are that environmental factors and crop specificity play an important role in the success of the interaction. However, to date, biofertilizers have typically met with limited success, often not proving to be efficacious under real farming conditions.

Therefore, there at least remains a need for improved compositions (including fertilizers) and methods which are effective in providing nutrients for plant growth, are environmentally safe, and/or are nonhazardous. It would be beneficial to provide a fertiliser composition and/or a plant growth medium for reducing pollution of the environment in combination with the reduction of economic costs.

It will be clearly understood that, if a prior art publication is referred to herein, this reference does not constitute an admission that the publication forms part of the common general knowledge in the art in Australia or in any other country.

SUMMARY OF INVENTION

In a first aspect of the present invention, there is provided a method of increasing plant growth, plant productivity, seed germination or soil quality for a dicotyledonous plant, or a monocotyledonous plant selected from wheat, rice, cotton and corn, the method comprising the step of: applying to the plant a treatment agent comprising at least one plant-beneficial *Burkholderia*-like species.

In another aspect of the present invention, there is provided a method of increasing plant growth, plant productivity, seed germination or soil quality for a dicotyledonous plant or a monocotyledonous plant, the method comprising the step of: applying to the plant a treatment agent comprising at least one plant-beneficial *Burkholderia*-like species.

In one embodiment, the at least one plant-beneficial *Burkholderia*-like species has at least 96% 16S rRNA sequence identity to Bacterium SOS3 (deposited on 2 Jun. 2016 under Accession No. V16/013910 at the National Measurement Institute, 1/153 Bertie Street Port Melbourne, Victoria, Australia 3207) or to *Burkholderia* strain Q208. In another embodiment, the at least one plant-beneficial *Burkholderia*-like species has at least 97%, 98% or 99% 16S rRNA sequence identity to Bacterium SOS3 or to *Burkholderia* strain Q208. In a further embodiment, the at least one plant-beneficial *Burkholderia*-like species has 100% 16S rRNA sequence identity to Bacterium SOS3 or to *Burkholderia* strain Q208. Bacterium SOS3 has 100% 16S rRNA sequence identity to *Burkholderia* strain Q208. The 16S rRNA sequence for Bacterium SOS3 is provided in SEQ ID No: 3. The sequence provided in SEQ ID No: 3 is also the 16S rRNA sequence for *Burkholderia* strain Q208.

In another embodiment, the at least one plant-beneficial *Burkholderia*-like species is at least one plant-beneficial *Burkholderia* species, at least one plant-beneficial-environment (PBE) *Burkholderia* species, or at least one species belong to the PBE clade of *Burkholderia* (see FIG. 1). The at least one plant-beneficial *Burkholderia*-like species may be non-pathogenic, especially a non-pathogenic *Burkholderia* species. The at least one plant-beneficial *Burkholderia*-like species is a bacteria.

The at least one plant-beneficial *Burkholderia*-like species may have an ability for (or be adapted to): (i) nitrogen fixation from atmospheric and/or (ii) forming biofilm on plant roots. The at least one plant-beneficial *Burkholderia*-like species may have an ability for (or be adapted to) solubilizing a source of phosphorous, especially at least one selected from the group consisting of: a phospholipid, a phosphoprotein, a phosphoester, a sugar phosphate and a phytate. The at least one plant-beneficial *Burkholderia*-like species may have an ability for (or be adapted to): (i) secretion of siderophores; and/or (ii) inducing ethylene production.

The at least one plant-beneficial *Burkholderia*-like species may be at least one bacterium selected from the group consisting of: Bacterium SOS1 (deposited on 2 Jun. 2016 under Accession No. V16/013908 at the National Measurement Institute, 1/153 Bertie Street Port Melbourne, Victoria, Australia 3207), Bacterium SOS2 (deposited on 2 Jun. 2016 under Accession No. V16/013909 at the National Measurement Institute, 1/153 Bertie Street Port Melbourne, Victoria, Australia 3207), Bacterium SOS3 (deposited on 2 Jun. 2016 under Accession No. V16/013910 at the National Measurement Institute, 1/153 Bertie Street Port Melbourne, Victoria, Australia 3207), *Burkholderia* strain Q208, *Burkholderia oxyphila, Burkholderia sacchari, Burkholderia ferrariae, Burkholderia silvatlantica, Burkholderia heleia, Burkholderia nodosa, Burkholderia bannensis, Burkholderia tropica, Burkholderia unamae, Burkholderia kururiensis, Burkholderia diazotrophica, Burkholderia tuberum, Burkholderia acidipaludis, Burkholderia caribensis, Burkholderia hospita, Burkholderia terrae, Burkholderia phymatum, Burkholderia sabiae, Burkholderia sartisoli, Burkholderia phenazinium, Burkholderia sediminicola, Burkholderia phytofirmans, Burkholderia ginsengisoli, Burkholderia fungorum, Burkholderia megapolitana, Burkholderia bryophila, Burkholderia terricola, Burkholderia graminis, Burkholderia phenoliruptrix, Burkholderia xenovorans, Burkholderia mimosarum, Burkholderia endofungorum, Burkholderia rhizoxinica, Burkholderia soli, Burkholderia caryophlii* and *Burkholderia caledonica*.

*Burkholderia* strain Q208 (also known as *Burkholderia australis, Burkholderia australis* Q208 or *Burkholderia* sp. Q208) was described in Paungfoo-Lonhienne et al. (ref. 10). Paungfoo-Lonhienne et al. isolated *Burkholderia* strain Q208 from the roots of Q208[4], a sugarcane variety, and illustrated that a *Burkholderia* strain Q208 isolate promotes growth of sugarcane plantlets. Paungfoo-Lonhienne et al. did not consider other strains of bacteria aside from *Burkholderia* strain Q208, nor growth enhancement mechanisms for plants other than sugarcane, nor seed germination enhancement for sugarcane or other plants.

The at least one plant-beneficial *Burkholderia*-like species may be at least one bacterium selected from the group consisting of: Bacterium SOS1, Bacterium SOS2, Bacterium SOS3 and *Burkholderia* strain Q208. In one embodiment, the at least one plant-beneficial *Burkholderia*-like species is at least one bacterium selected from the group consisting of: Bacterium SOS1, Bacterium SOS2 and Bacterium SOS3. In another embodiment, the at least one plant-beneficial *Burkholderia*-like species is *Burkholderia* strain Q208. In a further embodiment, the at least one plant-beneficial *Burkholderia*-like species is not *Burkholderia* strain Q208. The at least one plant-beneficial *Burkholderia*-like species may be isolated or derived from a microorganism belonging to the genus *Burkholderia*.

The at least one plant-beneficial *Burkholderia*-like species may be isolated from any suitable source. The at least one plant-beneficial *Burkholderia*-like species may be isolated from or adjacent to a monocotyledonous plant, especially a monocotyledonous plant selected from wheat, rice, cotton or corn. The at least one plant-beneficial *Burkholderia*-like species may be isolated from or adjacent to a dicotyledonous plant, especially a dicotyledonous plant including (or selected from) tomato, cucumber, beans, pea, broccoli, cabbage, soybean, cauliflower, lettuce, radish, strawberry or potato. The at least one plant-beneficial *Burkholderia*-like species may be isolated from the rhizosphere of a plant, especially from the rhizosphere of a monocotyledonous plant or dicotyledonous plant described above. In one embodiment, the at least one plant-beneficial *Burkholderia*-like species is isolated from the rhizosphere of a plant of the order of Solanales, especially Solanaceae (such as tomato). In one embodiment, the at least one plant-beneficial *Burkholderia*-like species is isolated form the rhizosphere of a tomato.

The at least one plant-beneficial *Burkholderia*-like species may be at least two species, at least three species, at least four species, at least five species or a plurality of species.

The treatment agent may further comprise one or more additional microorganisms that provide a synergy with the at least one plant-beneficial *Burkholderia*-like species. The one or more additional microorganisms may solubilise phosphorous. Exemplary microorganisms that solubilise phosphorous include one or more of: *Bacillus cereus, Aerobacter, Azotobacter, Aspergillus awamori, Penecillium* sp., *Rhizoctonia, Rhizopus, Torula thermophila, Sehwannio* and *Myces occidentalis*. Such microorganisms assist in providing additional phosphorous to plants.

The treatment agent may be a treatment composition. The treatment agent (or treatment composition) may be in any suitable form. In exemplary embodiments, the treatment agent (or treatment composition) may be in the form of a liquid, a gel or a solid, especially a sprayable liquid, a granule or a pellet.

The treatment agent may further comprise at least one plant nutrient. The at least one plant nutrient may include a source of phosphorous. The treatment agent (or treatment composition) may include a source of phosphorous. The source of phosphorous may be at least one of the group consisting of: a phospholipid, a phosphoprotein, a phosphoester, a sugar phosphate and a phytate. The at least one plant nutrient may also include an organic plant nutrient, especially manure or compost.

In one embodiment, the treatment agent (or treatment composition) is a microbial inoculant (for example as described below). In another embodiment, the treatment agent (or treatment composition) is a fertilizer composition (for example as described below). In yet another embodiment, the treatment agent (or treatment composition) is a soil-free growth medium (for example as described below). In a further embodiment, the treatment agent (or treatment composition) is a coating suitable for application to a plant seed (for example as described below).

The dicotyledonous plant may be any suitable dicotyledonous plant. In one embodiment, the dicotyledonous plant is selected from at least one of the group consisting of: tomato, cucumber, beans, pea, broccoli, cabbage, soybean, cauliflower, lettuce, radish, strawberry and potato.

The step of applying the treatment agent to the plant may comprise the step of applying the agent to the seeds or seedlings of the plant. The treatment agent may be applied to the plant in any suitable way. In one embodiment, the treatment agent may be sprayed or coated onto a seed or onto the roots of a seedling. In another embodiment, the treatment agent may be administered to the soil adjacent a plant (especially a seed or a seedling). In a further embodiment, the treatment agent may be applied to a growth medium (such as soil) into which the plant (especially a seed or seedling) is planted.

In one embodiment, the step of treating the seeds or seedlings comprises co-treatment with a source of phosphorous, especially at least one of the group consisting of: a phospholipid, a phosphoprotein, a phosphoester, a sugar phosphate and a phytate.

The method may further include the step of growing treated seeds or seedlings, especially in a soil-free growth medium. In this step, the treated seeds or seedlings may be grown into plantlets. In this step, the treated seeds or seedlings may be grown for an initial time period. The initial time period may be from 1 week to 6 weeks. The initial time period may be from 2 weeks to 6 weeks. In one embodiment, at least a part of the soil-free growth medium comprises the treatment agent (or treatment composition).

The method may further include the step of transferring the plantlets to a field or greenhouse conditions. In one embodiment, the transferred plantlets are cultivated in soil comprising fertiliser or manure. The method may further comprise the step of treating the soil or the manure with an additional amount of the treatment agent (or treatment composition).

In another aspect there is provided a method of promoting plant growth comprising:
   treating seeds or seedlings of a dicotyledonous plant, or a monocotyledonous plant selected from wheat, rice, cotton and corn, with an effective amount of a treatment composition (or treatment agent) comprising at least one plant-beneficial *Burkholderia*-like species;
   growing the treated seeds or seedlings in a soil-free growth medium for an initial time period to grow into plantlets; and
   transferring the plantlets to field or greenhouse conditions.

Features of this aspect of the invention may be as described above. In one embodiment of the method, the at least one plant-beneficial *Burkholderia*-like species is not *Burkholderia* strain Q208. In one embodiment, the at least one plant-beneficial *Burkholderia*-like species has at least 96% 16S rRNA sequence identity to Bacterium SOS3 (deposited on 2 Jun. 2016 under Accession No. V16/013910 at the National Measurement Institute, 1/153 Bertie Street Port Melbourne, Victoria, Australia 3207).

In another aspect there is provided a method of promoting plant growth comprising:
   treating seeds or seedlings of a dicotyledonous plant or a monocotyledonous plant, with an effective amount of a treatment composition (or treatment agent) comprising at least one plant-beneficial *Burkholderia*-like species;
   growing the treated seeds or seedlings in a soil-free growth medium for an initial time period to grow into plantlets; and
   transferring the plantlets to field or greenhouse conditions.

Features of this aspect of the invention may be as described above.

In one embodiment, at least a part of the soil-free growth medium comprises the treatment composition.

In another aspect, there is provided a microbial inoculant for increasing plant growth, plant productivity, seed germination or soil quality, the inoculant comprising: at least one plant-beneficial *Burkholderia*-like species. Features of this aspect of the present invention may be as described above. In one embodiment of the method, the at least one plant-beneficial *Burkholderia*-like species is not *Burkholderia* strain Q208. In one embodiment, the at least one plant-beneficial *Burkholderia*-like species has at least 96% 16S rRNA sequence identity to Bacterium SOS3 (deposited on 2 Jun. 2016 under Accession No. V16/013910 at the National Measurement Institute, 1/153 Bertie Street Port Melbourne, Victoria, Australia 3207).

However, in a preferred embodiment the present invention provides a microbial inoculant for increasing plant growth, plant productivity, seed germination or soil quality, the inoculant comprising: at least one bacterium selected from the group consisting of: Bacterium SOS1 (deposited on 2 Jun. 2016 under Accession No. V16/013908 at the National Measurement Institute, 1/153 Bertie Street Port Melbourne, Victoria, Australia 3207), Bacterium SOS2 (deposited on 2 Jun. 2016 under Accession No. V16/013909 at the National Measurement Institute, 1/153 Bertie Street Port Melbourne, Victoria, Australia 3207), Bacterium SOS3 (deposited on 2 Jun. 2016 under Accession No. V16/013910 at the National Measurement Institute, 1/153 Bertie Street Port Melbourne, Victoria, Australia 3207), *Burkholderia* strain Q208, *Burkholderia oxyphila, Burkholderia sacchari, Burkholderia ferrariae, Burkholderia silvatlantica, Burkholderia heleia, Burkholderia nodosa, Burkholderia bannensis, Burkholderia tropica, Burkholderia unamae, Burkholderia kururiensis, Burkholderia diazotrophica, Burkholderia tuberum, Burkholderia acidipaludis, Burkholderia caribensis, Burkholderia hospita, Burkholderia terrae, Burkholderia phymatum, Burkholderia sabiae, Burkholderia sartisoli, Burkholderia phenazinium, Burkholderia sediminicola, Burkholderia phytofirmans, Burkholderia ginsengisoli, Burkholderia fungorum, Burkholderia megapolitana, Burkholderia bryophila, Burkholderia terricola, Burkholderia graminis, Burkholderia phenoliruptrix, Burkholderia xenovorans, Burkholderia mimosarum, Burkholderia endofungorum, Burkholderia rhizoxinica, Burkholderia soli, Burkholderia caryophlii* and *Burkholderia caledonica.*

The at least one plant-beneficial *Burkholderia*-like species may be at least one bacterium selected from the group consisting of: Bacterium SOS1, Bacterium SOS2 and Bacterium SOS3 and *Burkholderia* strain Q208. In one embodiment, the at least one plant-beneficial *Burkholderia*-like species is at least one bacterium selected from the group consisting of: Bacterium SOS1, Bacterium SOS2 and Bacterium SOS3. In another embodiment, the at least one plant-beneficial *Burkholderia*-like species is *Burkholderia* strain Q208. In a further embodiment, the at least one plant-beneficial *Burkholderia*-like species is not *Burkholderia* strain Q208. The inoculant may further comprise *Burkholderia* strain Q208.

The microbial inoculant may be for use in (or be adapted to) increasing plant growth, plant productivity, seed germination or soil quality for a monocotyledonous plant selected from wheat, rice, cotton and corn and/or a dicotyledonous plant. The dicotyledonous plant may be as described above.

In a further aspect, the present invention provides a fertiliser composition comprising at least one plant-beneficial *Burkholderia*-like species. Features of this aspect of the present invention may be as described above.

In one embodiment, the at least one plant-beneficial *Burkholderia*-like species is at least one bacterium selected from the group consisting of: *Burkholderia* strain Q208, Bacterium SOS1, Bacterium SOS2 and Bacterium SOS3. In a further embodiment, the at least one plant-beneficial *Burkholderia*-like species is at least one bacterium selected from the group consisting of: Bacterium SOS1, Bacterium SOS2 and Bacterium SOS3. The at least one plant-beneficial *Burkholderia*-like species may be *Burkholderia* strain Q208. In a further embodiment, the at least one plant-beneficial *Burkholderia*-like species is not *Burkholderia* strain Q208.

The fertiliser composition may further comprise at least one plant nutrient. The at least one plant nutrient may be a source of phosphorous (as described above). The at least one plant nutrient may be manure or compost.

The fertiliser composition may be in any suitable form. In exemplary embodiments, the fertiliser composition may be in the form of a liquid or solid, especially a sprayable liquid, a granule or a pellet. The fertiliser composition may include manure or compost and be in the form of a pellet.

The fertiliser composition may be for use in (or be adapted to) increasing plant growth, plant productivity, seed germination or soil quality for a monocotyledonous plant selected from wheat, rice, cotton and corn and/or a dicotyledonous plant. The dicotyledonous plant may be as described above.

In another aspect, the present invention relates to a soil-free growth medium for growing seedlings comprising at least one plant-beneficial *Burkholderia*-like species. Features of this aspect of the present invention may be as described above.

The soil-free growth medium may further comprise at least one plant nutrient. The at least one plant nutrient may include a source of phosphorous. The source of phosphorus may be one or more of the group consisting of: a phospholipid, a phosphoprotein, a phosphoester, a sugar phosphate, and a phytate.

The soil-free growth medium may be in the form of a solid, a liquid or a gel.

According to a further aspect of the present invention, there is provided a coated plant seed, wherein the plant seed is coated with a coating comprising at least one plant-beneficial *Burkholderia*-like species.

The plant seed may be for a monocotyledonous plant, especially a monocotyledonous plant including (or selected from) wheat, rice, cotton and corn. The plant seed may be for a dicotyledonous plant. The dicotyledonous plant may be as described above.

The coating may be for (or be adapted to) increasing plant growth, plant productivity or seed germination of the plant seed, or be for (or be adapted to) improving the soil quality of the soil into which the plant seed is to be planted.

The coating may be applied in any suitable way. In one embodiment, the coating is applied by spraying the seed with a treatment agent comprising the at least one bacterium (such as a bacterial suspension). In another embodiment, the coating is applied by dipping the seed in a treatment agent comprising the at least one bacterium (such as a bacterial suspension).

In a further embodiment, the coating comprising a gelling agent. The gelling agent may include a polysaccharide (such as an alginate) or a gum (such as carboxymethylcellulose (CMC)).

In a further aspect, the present invention provides a method of increasing plant growth or increasing soil quality, the method comprising the step of: applying to a plant a microbial inoculant or a fertiliser composition as described above.

In another aspect, the present invention provides a microbial inoculant for use in increasing plant growth or seed germination or plant productivity or increasing soil quality for monocotyledonous plants selected from wheat, rice, cotton, corn and/or dicotyledonous plants including one or more of tomato, cucumber, beans, pea, broccoli, cabbage, soybean, cauliflower, lettuce, radish, strawberry, potato; the inoculant comprising: Bacterium SOS1, Bacterium SOS2, Bacterium SOS3, or *Burkholderia* strain Q208 isolated or derived from a microorganism belonging to the genus *Burkholderia*. In a further aspect of the present invention, there is provided a microbial inoculant for use in increasing plant growth or seed germination or plant productivity or increasing soil quality for monocotyledonous plants including one or more of wheat, rice, cotton, wheat, corn and/or dicotyledonous plants including one or more of tomato, cucumber, beans, pea, broccoli, cabbage, soybean, cauliflower, lettuce, radish, strawberry, potato; comprising a microorganism Bacterium SOS1, Bacterium SOS2, Bacterium SOS3, or belonging to the genus *Burkholderia* and having an ability for:

(i) nitrogen fixation from atmospheric air; and (ii) forming biofilm on plant roots.

Preferably, the microorganism may also have the ability for solubilizing phospholipids and/or phosphoproteins and/or phosphoesters and/or sugar phosphates and/or phytate.

Preferably, the microorganism may also have the ability for:

(iii) secretion of siderophores; and/or (iv) inducing ethylene production.

In some embodiments, the microorganism may be *Burkholderia* strain Q208.

In some further embodiments, the inoculant may comprise strains from one or more of the following bacterial species: Bacterium SOS1 (deposited on 2 Jun. 2016 under Accession No. V16/013908 at the National Measurement Institute, 1/153 Bertie Street Port Melbourne, Victoria, Australia 3207), Bacterium SOS2 (deposited on 2 Jun. 2016 under Accession No. V16/013909 at the National Measurement Institute, 1/153 Bertie Street Port Melbourne, Victoria, Australia 3207), Bacterium SOS3 (deposited on 2 Jun. 2016 under Accession No. V16/013910 at the National Measurement Institute, 1/153 Bertie Street Port Melbourne, Victoria, Australia 3207), *Burkholderia* strain Q208, *Burkholderia oxyphila*, *Burkholderia sacchari*, *Burkholderia ferrariae*,

*Burkholderia silvatlantica, Burkholderia heleia, Burkholderia nodosa, Burkholderia bannensis, Burkholderia tropica, Burkholderia unamae, Burkholderia kururiensis, Burkholderia diazotrophica, Burkholderia tuberum, Burkholderia acidipaludis, Burkholderia caribensis, Burkholderia hospita, Burkholderia terrae, Burkholderia phymatum, Burkholderia sabiae, Burkholderia sartisoli, Burkholderia phenazinium, Burkholderia sediminicola, Burkholderia phytofirmans, Burkholderia ginsengisoli, Burkholderia fungorum, Burkholderia megapolitana, Burkholderia bryophila, Burkholderia terricola, Burkholderia graminis, Burkholderia phenoliruptrix, Burkholderia xenovorans*, and *Burkholderia caledonica*, or a mixture thereof. In one embodiment, said mixture further comprises one or more additional microorganisms that provide a synergy with the bacterial species. The one or more additional microorganisms may solubilise phosphorous. Exemplary microorganisms that solubilise phosphorous include one or more of: *Bacillus cereus, Aerobacter, Azotobacter, Aspergillus awamori, Penecillium* sp., *Rhizoctonia, Rhizopus, Torula thermophila, Sehwannio* and *Myces occidentalis*. Such microorganisms assist in providing additional phosphorous to plants.

In further aspect of the present invention, there is provided a fertiliser composition comprising a microbial inoculant comprising one or more of *Burkholderia australis* strain Q208, Bacterium SOS1, Bacterium SOS2 and Bacterium SOS3 isolated or derived from a microorganism belonging to the genus *Burkholderia*.

In another aspect of the invention, there is provided a fertiliser composition comprising a microorganism Bacterium SOS1, Bacterium SOS2, Bacterium SOS3, or belonging to the genus *Burkholderia* and having an ability for:

(i) nitrogen fixation from atmospheric air; and (ii) forming biofilm on plant roots.

Preferably, the microorganism may have the ability for solubilizing phospholipids and/or phosphoproteins and/or phosphoesters and/or sugar phosphates and/or phytate.

Preferably, the microorganism may also have the ability for:

(iii) secretion of siderophores; and/or (iv) inducing ethylene production.

In some embodiments, the fertiliser composition may further comprise one or more of the following: phospholipids, phosphoproteins, phosphoesters, sugar phosphates, and phytate.

In some further embodiments, the fertiliser may further comprise organic fertilisers comprising manure or compost.

In some embodiments, the microorganism may comprise one or more of *Burkholderia australis* Q208, Bacterium SOS1, Bacterium SOS2 and Bacterium SOS3.

In some further embodiments, the fertiliser may comprise strains from one or more of the following bacterial species: Bacterium SOS1, Bacterium SOS2, Bacterium SOS3, *Burkholderia* strain Q208, *Burkholderia oxyphila, Burkholderia sacchari, Burkholderia ferrariae, Burkholderia silvatlantica, Burkholderia heleia, Burkholderia nodosa, Burkholderia bannensis, Burkholderia tropica, Burkholderia unamae, Burkholderia kururiensis, Burkholderia diazotrophica, Burkholderia tuberum, Burkholderia acidipaludis, Burkholderia caribensis, Burkholderia hospita, Burkholderia terrae, Burkholderia phymatum, Burkholderia sabiae, Burkholderia sartisoli, Burkholderia phenazinium, Burkholderia sediminicola, Burkholderia phytofirmans, Burkholderia ginsengisoli, Burkholderia fungorum, Burkholderia megapolitana, Burkholderia bryophila, Burkholderia terricola, Burkholderia graminis, Burkholderia phenoliruptrix, Burkholderia xenovorans*, and *Burkholderia caledonica* or a mixture thereof. In one embodiment, said mixture further comprises one or more additional microorganisms that provide a synergy with the bacterial species. The one or more additional microorganisms may solubilise phosphorous. Exemplary microorganisms that solubilise phosphorous include one or more of: *Bacillus cereus, Aerobacter, Azotobacter, Aspergillus awamori, Penecillium* sp., *Rhizoctonia, Rhizopus, Torula thermophila, Sehwannio* and *Myces occidentalis*. Such microorganisms assist in providing additional phosphorous to plants.

In an embodiment, the fertiliser is adapted for use in increasing plant growth or plant productivity or increasing soil quality in monocotyledonous plants including one or more of wheat, rice, cotton, wheat, corn and/or dicotyledonous plants including one or more of tomato, cucumber, beans, pea, broccoli, cabbage, soybean, cauliflower, lettuce, radish; strawberry, potato.

In another aspect of the present invention, there is provided a soil-free growth medium for growing seedlings comprising one or more of *Burkholderia australis* strain Q208, Bacterium SOS1, Bacterium SOS2 and Bacterium SOS3 isolated or derived from microorganism belonging to the genus *Burkholderia.*

In a further aspect, there is provided a soil-free growth medium for growing and/or germinating seedlings comprising a microorganism Bacterium SOS1, Bacterium SOS2, Bacterium SOS3, or belonging to the genus *Burkholderia* and having an ability for:

(i) nitrogen fixation from atmospheric air; and (ii) forming biofilm on plant roots.

Preferably, the microorganism may have the ability for solubilizing phospholipids and/or phosphoproteins and/or phosphoesters and/or sugar phosphates and/or phytate.

In some embodiments, the microorganism may also have the ability for:

(iii) secretion of siderophores; and/or (iv) inducing ethylene production.

In some embodiments, the soil-free growth medium may further comprise one or more of the following: phospholipids, phosphoproteins, phosphoesters, sugar phosphates, and phytate.

In some embodiments, the growth medium may comprise strains from one or more of the following bacterial species: Bacterium SOS1, Bacterium SOS2, Bacterium SOS3, *Burkholderia* strain Q208, *Burkholderia oxyphila, Burkholderia sacchari, Burkholderia ferrariae, Burkholderia silvatlantica, Burkholderia heleia, Burkholderia nodosa, Burkholderia bannensis, Burkholderia tropica, Burkholderia unamae, Burkholderia kururiensis, Burkholderia diazotrophica, Burkholderia tuberum, Burkholderia acidipaludis, Burkholderia caribensis, Burkholderia hospita, Burkholderia terrae, Burkholderia phymatum, Burkholderia sabiae, Burkholderia sartisoli, Burkholderia phenazinium, Burkholderia sediminicola, Burkholderia phytofirmans, Burkholderia ginsengisoli, Burkholderia fungorum, Burkholderia megapolitana, Burkholderia bryophila, Burkholderia terricola, Burkholderia graminis, Burkholderia phenoliruptrix, Burkholderia xenovorans*, and *Burkholderia caledonica* or a mixture thereof. In one embodiment, said mixture further comprises one or more additional microorganisms that provide a synergy with the bacterial species. The one or more additional microorganisms may solubilise phosphorous. Exemplary microorganisms that solubilise phosphorous include one or more of: *Bacillus cereus, Aerobacter, Azotobacter, Aspergillus awamori, Penecillium* sp., *Rhizoc-* tonia, *Rhizopus, Torula thermophila, Sehwannio* and *Myces occidentalis*. Such microorganisms assist in providing additional phosphorous to plants.

In some embodiments, the growth medium may comprise one or more of *Burkholderia australis* Q208, Bacterium SOS1, Bacterium SOS2 and Bacterium SOS3.

In some embodiments, the soil-free growth medium may be adapted for growing seedlings for monocotyledonous plants including one or more of rice, cotton, wheat, corn and/or dicotyledonous plants including one or more of tomato, cucumber, beans, pea, broccoli, cabbage, soybean, cauliflower, lettuce, radish, strawberry, potato.

In a further aspect of the present invention, there is provided a method of promoting plant growth comprising:

treating seeds or seedlings with an effective amount of a treatment composition comprising one or more of Bacterium SOS1, Bacterium SOS2, Bacterium SOS3 and *Burkholderia* strain Q208, isolated or derived from a microorganism belonging to the genus *Burkholderia*;

growing the treated seeds or seedlings in a soil-free growth medium for an initial time period to grow into plantlets; and transferring the plantlets to field or greenhouse conditions.

In an further aspect of the present invention, there is provided method of promoting plant growth comprising:

treating seeds or seedlings with an effective amount of a treatment composition comprising a microorganism Bacterium SOS1, Bacterium SOS2, Bacterium SOS3, or belonging to the genus *Burkholderia* and having an ability for:

a. nitrogen fixation from atmospheric air; and
b. forming biofilm on plant roots;
c. growing the treated seeds or seedlings Preferably, the microorganism also has the ability for solubilizing phospholipids and/or phosphoproteins and/or phosphoesters and/or sugar phosphates and/or phytate.

In some embodiments, the microorganism may have the ability for:

(i) secretion of siderophores; and/or
(ii) inducing ethylene production.

In some embodiments, the step of growing the treated seeds or seedlings comprises: growing said seeds or seedlings in a soil-free growth medium for an initial time period to grow into plantlets; and transferring the plantlets to field or greenhouse conditions.

In some embodiments, at least a part of the soil-free growth medium comprises the treatment composition.

In some embodiments, the initial time period ranges from 1 week to 6 weeks and more preferably from 2 weeks to 6 weeks.

In some embodiments, the transferred plantlets are cultivated in soil comprising organic fertiliser or manure or compost.

In some embodiments, the step of treating the soil or the manure with an additional amount of the treatment composition. Preferably, the step of treating with the treatment composition further comprises co-treatment with phospholipids and/or phosphoproteins and/or phosphoesters and/or sugar phosphates and/or phytate.

In some embodiments of the method, the treatment composition comprises strains from one or more of the following bacterial species: Bacterium SOS1, Bacterium SOS2, Bacterium SO53, *Burkholderia* strain Q208, *Burkholderia oxyphila, Burkholderia sacchari, Burkholderia ferrariae, Burkholderia silvatlantica, Burkholderia heleia, Burkholderia nodosa, Burkholderia bannensis, Burkholderia tropica, Burkholderia unamae, Burkholderia kururiensis, Burkholderia diazotrophica, Burkholderia tuberum, Burkholderia acidipaludis, Burkholderia caribensis, Burkholderia hospita, Burkholderia terrae, Burkholderia phymatum, Burkholderia sabiae, Burkholderia sartisoli, Burkholderia phenazinium, Burkholderia sediminicola, Burkholderia phytofirmans, Burkholderia ginsengisoli, Burkholderia fungorum, Burkholderia megapolitana, Burkholderia bryophila, Burkholderia terricola, Burkholderia graminis, Burkholderia phenoliruptrix, Burkholderia xenovorans*, and *Burkholderia caledonica*, or a mixture thereof. In one embodiment said mixture further one or more additional microorganisms that provide a synergy with the strains of the bacterial species. The one or more additional microorganisms may solubilise phosphorous. Exemplary microorganisms that solubilise phosphorous include one or more of: *Bacillus cereus, Aerobacter, Azotobacter, Aspergillus awamori, Penecillium* sp., *Rhizoctonia, Rhizopus, Torula thermophila, Sehwannio* and *Myces occidentalis*. Such microorganisms assist in providing additional phosphorous to plants.

In some embodiments of the method, the treatment composition may comprise one or more of *Burkholderia australis* Q208, Bacterium SOS1, Bacterium SOS2 and Bacterium SOS3.

In some embodiments, the method may be adapted for promoting plant growth for monocotyledonous plants including one or more of wheat, rice, cotton, wheat, corn and/or dicotyledonous plants including one or more of tomato, cucumber, beans, pea, broccoli, cabbage, soybean, cauliflower, lettuce, radish, strawberry, potato.

In some embodiments, the method may be adapted for promoting seed germination for monocotyledonous plants including one or more of wheat, rice, cotton, wheat, corn and/or dicotyledonous plants including one or more of tomato, cucumber, beans, pea, broccoli, cabbage, soybean, cauliflower, lettuce, radish, strawberry, potato.

Definitions of specific embodiments of the invention as claimed herein follow.

According to a first embodiment of the invention, there is provided a method of increasing plant growth, plant productivity, seed germination or soil quality for a dicotyledonous plant, or a monocotyledonous plant selected from wheat, rice, cotton and corn, the method comprising the step of: applying to the plant a treatment agent comprising at least one plant-beneficial *Burkholderia*-like species, wherein the at least one plant-beneficial *Burkholderia*-like species has at least 97% 16S rRNA sequence identity to Bacterium SOS3 (deposited on 2 Jun. 2016 under Accession No. V16/013910 at the National Measurement Institute, 1/153 Bertie Street Port Melbourne, Victoria, Australia 3207), and configured to form biofilms on the roots of the plant.

According to a second embodiment of the invention, there is provided a method of promoting plant growth comprising:

treating seeds or seedlings of a dicotyledonous plant, or a monocotyledonous plant selected from wheat, rice, cotton and corn, with an effective amount of a treatment agent comprising at least one plant-beneficial *Burkholderia*-like species, wherein the at least one plant-beneficial *Burkholderia*-like species has at least 97% 16S rRNA sequence identity to Bacterium SOS3 (deposited on 2 Jun. 2016 under Accession No. V16/013910 at the National Measurement Institute, 1/153 Bertie Street Port Melbourne, Victoria, Australia 3207), and is configured to form biofilms on the roots of the seedlings or seedlings grown from the seeds;

growing the seeds or seedlings in a soil-free growth medium for an initial time period to grow into plantlets; and transferring the plantlets to field or greenhouse conditions.

According to a third embodiment of the invention, there is provided a microbial inoculant when used for increasing plant growth, plant productivity, seed germination or soil quality of a dicotyledonous plant, or a monocotyledonous plant selected from wheat, rice, cotton and corn, the inoculant comprising: at least one bacterium selected from the group consisting of: Bacterium SOS3 (deposited on 2 Jun. 2016 under Accession No. V16/013910 at the National Measurement Institute, 1/153 Bertie Street Port Melbourne, Victoria, Australia 3207), *Burkholderia oxyphila*, *Burkholderia sacchari*, *Burkholderia ferrariae*, *Burkholderia heleia* and *Burkholderia bannensis*, wherein said at least one bacterium is configured to form biofilms on the roots of plants grown or germinated from seeds or in soil treated with the microbial inoculant.

According to a fourth embodiment of the invention, there is provided a fertiliser composition when used for increasing plant growth, plant productivity, seed germination or soil quality for a dicotyledonous plant, or a monocotyledonous plant selected from wheat, rice, cotton and corn, said composition comprising at least one bacterium selected from the group consisting of: at least one plant-beneficial *Burkholderia*-like species, wherein the at least one plant-beneficial *Burkholderia*-like species has at least 97% 16S rRNA sequence identity to Bacterium SOS3 (deposited on 2 Jun. 2016 under Accession No. V16/013910 at the National Measurement Institute, 1/153 Bertie Street Port Melbourne, Victoria, Australia 3207), and configured to form biofilms on the roots of plants treated with the fertilizer composition.

According to a fifth embodiment of the invention, there is provided a soil-free growth medium when used for growing seedlings of a dicotyledonous plant, or a monocotyledonous plant selected from wheat, rice, cotton and corn, said medium comprising at least one bacterium selected from the group consisting of: at least one plant-beneficial *Burkholderia*-like species, wherein the at least one plant-beneficial *Burkholderia*-like species has at least 97% 16S rRNA sequence identity to Bacterium SOS3 (deposited on 2 Jun. 2016 under Accession No. V16/013910 at the National Measurement Institute, 1/153 Bertie Street Port Melbourne, Victoria, Australia 3207), and is configured to form biofilms on the roots of seedlings grown in the soil-free growth medium.

According to a sixth embodiment of the invention, there is provided a coated plant seed of a dicotyledonous plant, or a monocotyledonous plant selected from wheat, rice, cotton and corn, wherein the plant seed is coated with a coating comprising at least one bacterium selected from the group consisting of: at least one plant-beneficial *Burkholderia*-like species, wherein the at least one plant-beneficial *Burkholderia*-like species has at least 97% 16S rRNA sequence identity to Bacterium SOS3 (deposited on 2 Jun. 2016 under Accession No. V16/013910 at the National Measurement Institute, 1/153 Bertie Street Port Melbourne, Victoria, Australia 3207), and is configured to form biofilms on the roots of a seedling grown from the coated plant seed.

According to a seventh embodiment of the invention, there is provided a method of increasing plant growth or plant productivity or increasing soil quality, the method comprising the step of: applying to a plant the microbial inoculant according to the third embodiment.

Any of the features described herein can be combined in any combination with any one or more of the other features described herein within the scope of the invention.

BRIEF DESCRIPTION OF THE DRAWINGS

Various embodiments of the invention will be described with reference to the following drawings, in which.

Figure 1:
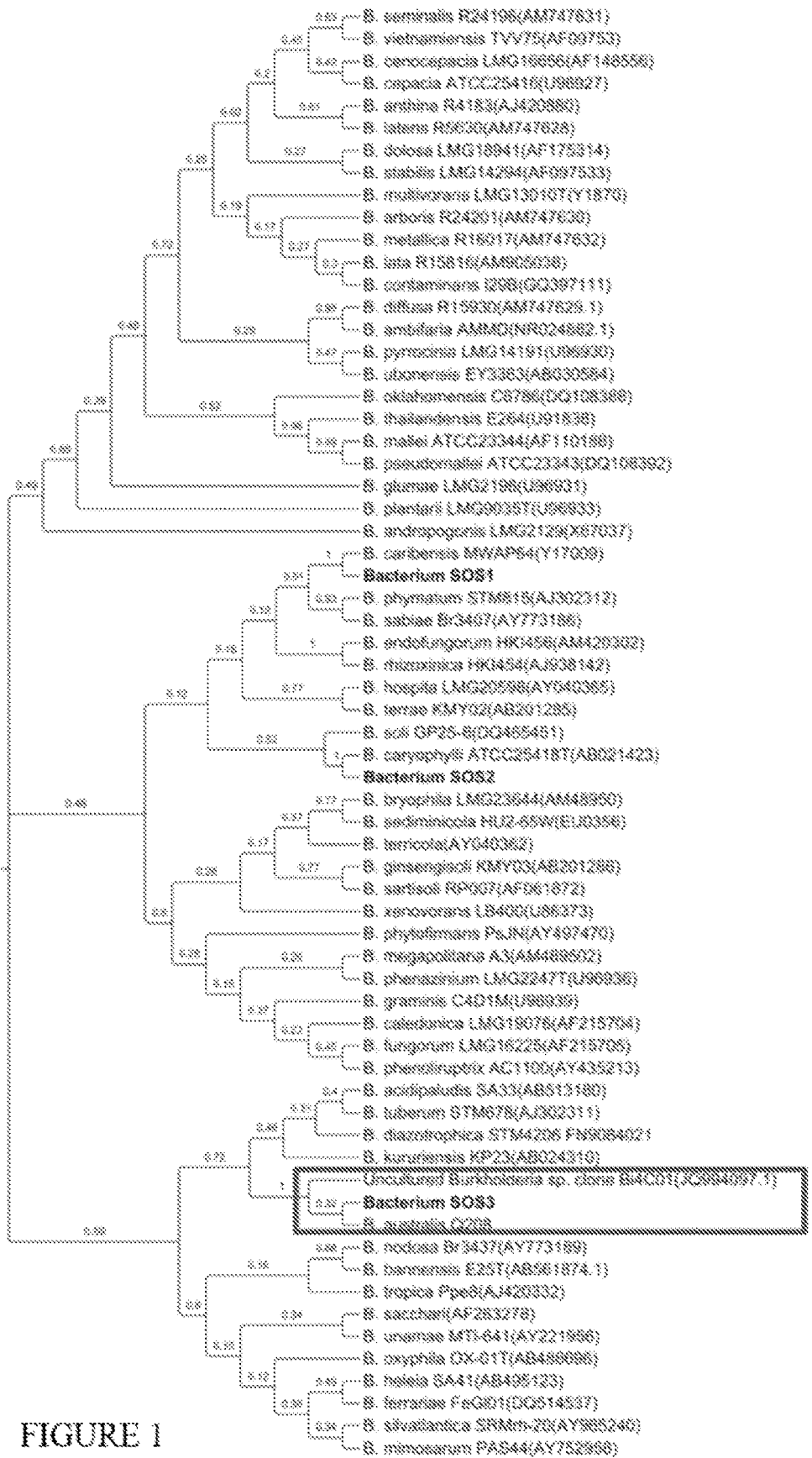
FIG. 1 illustrates a phylogenetic tree of 16S rRNA gene sequences showing the position of strains Bacterium SOS1, Bacterium SOS2, and Bacterium SO3 within the PBE clade of *Burkholderia*.

Preferred features, embodiments and variations of the invention may be discerned from the following Description of Embodiments and Examples which provides sufficient information for those skilled in the art to perform the invention. The following Description of Embodiments and Examples are not to be regarded as limiting the scope of the preceding Summary of the Invention in any way.

DESCRIPTION OF EMBODIMENTS

The invention in at least some embodiments relates to isolating a microorganism such as bacterium *B. australis*, Bacterium SOS1, Bacterium SOS2 or Bacterium SOS3 from the rhizosphere of plants and the disclosure encompasses methods for isolating microorganisms as previously discussed. Plant-beneficial *Burkholderia*-like species may have beneficial physiological characteristics including and ability for: (i) nitrogen fixation from atmospheric air; (ii) forming biofilm on plant roots; (iii) solubilising phospholipids and/or phosphoproteins and/or phosphoesters and/or sugar phosphates and/or phytate; (iv) secretion of siderophores; and/or (v) inducing ethylene production. In some experiments, plant-beneficial *Burkholderia*-like species (which may include bacteria exhibiting similar physiological characteristics as *B. australis* Q208, Bacterium SOS1, Bacterium SOS2 and Bacterium SOS3 (denoted by *B. australis* Q208 and related species-BARS), and which may include other bacteria belonging to PBE clade of *Burkholderia* (referred to collectively as *Burkholderia* Related Species—BRS)) have been considered in further detail. It is expected that the physiological characteristics of BRS are similar to those of BARS. BARS and BRS can be identified via application of the following primers:—OTU11burkhold_R: (GTTGGCAACCCTCTGTTC) and—926F: (AAAC-TYAAAKGAATTGACGG (Y corresponds to C or T; K corresponds to G or T)) as described in Paungfoo-Lonhienne et al (ref. 10).

Preliminary experiments conducted by the present inventors indicate that BARS and BRS enhance seed germination and growth of a wide variety of plants, including Solanaceae (e.g. tomato, potato) Poaceae (e.g. rice, wheat, and maize). Without being bound by theory, it is theorised that BRS and BARS have the ability to i) assimilate phosphorus from a number of hardly-degradable, inorganic and organic compounds, ii) trigger production of ethylene in plants, and iii) secrete siderophores.

The applicants theorise that BARS and BRS have the ability to fix nitrogen from the air. BARS and BRS localize in the rhizosphere and fix atmospheric nitrogen via a new, not revealed yet molecular pathway.

The applicants also theorise that BARS and BRS have the ability to extract phosphorus from organic fertilizers or phospholipids, phosphoproteins, phosphoesters, sugar phosphates, and phytate (commonly referred here as PRC). Plant tissues and organic fertilizers (i.e. manure and compost) contain high amount of hardly-degradable and highly phosphorus-enriched compounds. As PRC are highly abundant in manure and compost, the ability of BARS and BRS to utilize these compounds represents a great possibility to significantly reduce agricultural expenses worldwide, reducing the need for high amount of mineral phosphorus. BARS may also be able to solubilize some inorganic forms of phosphorus (i.e. calcium phosphate) that are hardly accessible for plants, but present in high concentration in soil (ref. 9).

The applicants also theorise that BARS and BRS exhibit protective effect against pathogenic microorganisms, forming a biofilm around plant roots. This diminishes the possibility of root colonization by pathogenic microorganisms.

The applicants also theorise that association of a plant with BARS or BRS triggers production of ethylene in plants. Ethylene is an efficient agent against nematodes. Nematodes are responsible for tremendous loss of crops. For example, *Hirschmanniella oryzae*, i.e. rice root nematode (RRN), is among the major pests of rice and is the most common plant-parasitic nematode found on irrigated rice. Accordingly, by inducing ethylene production in plants, treatment of plants with BARS or BRS renders plants more resilient to nematodes.

Upon association with plants, it is believed that BARS and BRS secrete siderophores. Siderophores scavenge iron from minerals creating a soluble form of this element. Many plants are able to assimilate iron via these microbial siderophores (ref. 11). Thus, this is another important feature of BARS and BRS, which can be beneficial in soils poor for easily-accessible iron.

Bacterium SOS1 has about 98% 16S rRNA sequence identity to the strain *Burkholderia* sp. Q208. Bacterium SOS2 has about 99% 16S rRNA sequence identity to the strain *Burkholderia* sp. Q208. Bacterium SOS3 has about 100% 16S rRNA sequence identity to the strain *Burkholderia* sp. Q208. Sequencing analyses conducted in the prior art have shown that these bacteria do not possess the determinants of pathogenicity, such as specific clusters of genes coding for T3SS3 and T4SS.

BRS may be isolated by screening bacteria in plant rizosphere or soil, or other media, by using 16S rRNA primers specific to *Burkholderia* sp. Q208.

BARS and BRS may be exposed to seeds or seedlings, for a brief period of time before transferring the plants into the soil or other growth media. In one embodiment, the seeds or seedlings are soaked in a suspension containing BRS or BARS. The brief soaking of seeds or seedlings into the bacterial suspension for an initial time period is sufficient to initiate improved growth and disease-suppressive characteristics. The seeds treated with BRS or BARS may be germinated in soil or in a soil-free growth medium as discussed in previous sections.

The method of promoting plant growth as discussed in previous sections in some embodiments relies on protecting plant roots from pathogens. This embodiment is based on an expected ability of BARS and BRS to form biofilm on plant roots and stimulate production of ethylene in plants. The formation of the biofilm impedes other microorganisms such as bacteria and fungi to colonize the roots. The method may also promote the production of ethylene which assists in protecting plants from nematodes.

The present disclosure provides a number of methods for treatment of seeds, seedlings, plantlets, and plants with BRS and BARS, and compositions for delivery of BRS and BARS into soil and hydroculture media. In an embodiment, seedlings may be grown in a soil-free media containing BRS or BARS for a period of 2-6 weeks and then transplanted to field or greenhouse conditions. This method may allow seedlings to grow in an optimized growth medium, which is chosen in function of the plant's specific requirement. PRC may be an additive that strongly increases the efficiency of the plant-*Burkholderia* (or, more specifically, plant-BRS) association. This method may provide young plants with improved physical characteristics, such as greater height and weight, increased root system, and increased health, compared to control plants. The outcome may be that plants reach a mature stage earlier and provide better yield.

Seeds may be treated with BRS or BARS via spray or dipping, such as spraying or dipping a bacterial suspension onto the seeds, before transferring the seeds into the growth media. This method may stimulate growth at the early seedling stage which increases the seeding's vigour, ultimately leading to higher yields.

Alternatively, seeds may be coated with a solution of alginate (2% w/v) or CMC (4% w/v). The solutions can be prepared by dissolving powder in distilled water at room temperature, agitating the solution and autoclaving at 121° C. for 20 minutes. Seeds may then be coated in the solution containing BRS and are subsequently air dried.

Seeds and seedling which may be treated, include the whole spectrum of both monocotyledonous and dicotyledonous plant species selected from rice, cotton, wheat, corn, tomato, cucumber, beans, pea, broccoli, cabbage, soybean, cauliflower, lettuce, radish; strawberry etc. In general, any seed or seedling which responds to the acting component (BRS or BARS) of the invention may be treated in accordance with the invention.

The present disclosure, in another embodiment, offers the methods of combined treatment of soil and hydroculture with BRS or BARS, and manure or compost. Applying animal manure or compost to farmland constitutes environmentally sound management of soil. Bacteria require nitrogen, phosphorus and other chemical elements for their metabolism. BRS and BARS, which have the ability to metabolise organic molecules that contain high concentration of these elements, not only use the product for their own development, but also render organic chemical elements available for the plant. The applicants have found that addition of manure to the growth medium containing BARS or BRS greatly enhances plant growth and fitness, compared to the plants grown only in the presence of manure.

BRS or BARS may be mixed with manure and compost according to known agricultural practises in the form of dry pellets. This method may enrich the soil with BRS or BARS durably, stimulating growth and fitness of plants for their entire life cycle.

Another compound that may be used for co-treatment with BARS or BRS is PRC (phospholipids, phosphoproteins, phosphoesters, sugar phosphates, and phytate). Any of the PRC compounds may be used separately or in different combinations. Addition of PRC to the growth medium containing BARS or BRS may enhance plant growth and fitness at the early stage of plant growth. The combination of BRS or BARS with one or few compounds from the PRC list may be included in the feeding media for growth of hydroponic culture. It is envisaged that the present disclosure will result in great economical effect. PRC compounds are relatively cheap components and represent a renewable source of phosphorus. PRC which are present in high amounts in plant tissues and acting as phosphorus storage are highly available in compost of animal manure. Its use is an environmentally friendly process, occurring without damaging of phosphate rocks.

The diverse group of *Burkholderia* may be re-classified and a separate genus may appear in the bacterial taxonomy which will include the microorganisms currently belonging to the PBE *Burkholderia* clade. The PBE group of *Burkholderia* is separate from the pathogenic group (see FIG. 1), and the bacteria having at least 96% 16S rRNA sequence identity to the strain *Burkholderia* sp. Q208 and Bacterium SOS3 belong to the PBE, clade. Plant-beneficial *Burkholderia*-like species include such bacteria. Currently this environmental Blade includes such representatives as: Bacterium SOS1, Bacterium SOS2, Bacterium SOS3, *Burkholderia* sp. Q208, *Burkholderia oxyphila*, *Burkholderia sacchari*, *Burkholderia ferrariae*, *Burkholderia silvatlantica*, *Burkholderia heleia*, *Burkholderia nodosa*, *Burkholderia bannensis*, *Burkholderia tropica*, *Burkholderia unamae*, *Burkholderia kururiensis*, *Burkholderia diazotrophica*, *Burkholderia tuberum*, *Burkholderia acidipaludis*, *Burkholderia caribensis*, *Burkholderia hospita*, *Burkholderia terrae*, *Burkholderia phymatum*, *Burkholderia sabiae*, *Burkholderia sartisoli*, *Burkholderia phenazinium*, *Burkholderia sediminicola*, *Burkholderia phytofirmans*, *Burkholderia ginsengisoli*, *Burkholderia fungorum*, *Burkholderia megapolitana*, *Burkholderia bryophila*, *Burkholderia terricola*, *Burkholderia graminis*, *Burkholderia phenoliruptrix*, *Burkholderia xenovorans*, and *Burkholderia caledonica*. FIG. 1 provides a phylogenetic tree of 16S rRNA gene sequences showing the position of strains Bacterium SOS1, SOS2, and SO3 within the PBE clade of *Burkholderia*. The consensus tree topology was inferred using neighbour-joining with nonparametric bootstrap based on maximum composite likelihood (1000 replicates; MEGA v5.05). Bootstrap support value ≥50% is shown a teach internal node. Thick branches indicate Bayesian posterior probabilities ≥0.90. Unit of branch length is in number of substitutions per site. Boxed area indicates *Burkholderia australis* Q208-related strains, which have 100% sequence identity by 16S rRNA sequence comparison, this group includes Bacterium SOS3. All other PBE bacteria which have at least 96% 16S rRNA sequence identity to *Burkholderia australis* Q208 are indicated within the text as BRS (*Burkholderia*-related strains), and Bacterium SOS1 and Bacterium SOS2 belong to this group.

In the present specification and claims (if any), the word 'comprising' and its derivatives including 'comprises' and 'comprise' include each of the stated integers but does not exclude the inclusion of one or more further integers.

Reference throughout this specification to 'one embodiment' or 'an embodiment' means that a particular feature, structure, or characteristic described in connection with the embodiment is included in at least one embodiment of the present invention. Thus, the appearance of the phrases 'in one embodiment' or 'in an embodiment' in various places throughout this specification are not necessarily all referring to the same embodiment. Furthermore, the particular features, structures, or characteristics may be combined in any suitable manner in one or more combinations.

In compliance with the statute, the invention has been described in language more or less specific to structural or methodical features. It is to be understood that the invention is not limited to specific features shown or described since the means herein described comprises preferred forms of putting the invention into effect. The invention is, therefore, claimed in any of its forms or modifications within the proper scope of the appended claims (if any) appropriately interpreted by those skilled in the art.

EXAMPLES

The following examples are illustrative of one or more exemplary embodiments of the invention and should not be construed as limiting in any way the general nature of the disclosure of the description throughout this specification.

Example 1—Microbial Strains and Maintenance of Culture

Microbial Strains.

The following microbial strains were used for treatment of seeds, seedlings and plants, and in the production of biofertilisers: *Burkholderia australis* Q208, Bacterium SOS1, Bacterium SOS2 and Bacterium SOS3 (BARS). Bacterium SOS1, Bacterium SOS2 and Bacterium SOS3 were isolated from the sugar cane and rice rhizospheres (in the case of *Burkholderia australis* Q208) and tomato rhizospheres (in the case of Bacterium SOS1, Bacterium SOS2 and Bacterium SOS3). Partial 16S rRNA sequencing indicated that the strains belong to the Plant-Beneficial-Environment (PBE) *Burkholderia* clade. Full sequencing of DNA confirmed that these bacteria are non-pathogenic microorganisms as they lack necessary genes for pathogenicity such as coding for components of T3SS and T4SS systems. When cultured aerobically on R2A media with the addition of phytate for 2 days at 28° C., BARS produce non-mucoid small and mucoid big colonies. Cells are Gram-negative, non-spore-forming and ovoids to short rods (0.4-0.5 μm in width and 1.0±1.3 μm in length), and occur singly or in pairs. Physiologically the bacteria are β-Galactosidase, catalase and oxidase positive, not producing indole, not hydrolysing gelatin and not fermenting glucose. The DNA G+C content is around 63.3 mol %. Bacterium SOS1, Bacterium SOS2 and Bacterium SOS3 represent rod-shaped cells, form white colonies on R2A medium, entire margin, and are Gram negative. The tested morphological and physiological characteristics of Bacterium SOS1, Bacterium SOS2 and Bacterium SOS3 are similar to the other representatives of the genus *Burkholderia*: the cells are motile, non-fermentative and non-fluorescent, and are resistant to ampicillin, but not to kanamycin. Bacterium SOS1, Bacterium SOS2 and Bacterium SOS3 are negative in the arginine dihydrolase test. The cDNA sequence corresponding to the 16S rRNA sequence of Bacterium SOS1 is provided in SEQ ID No: 1, the cDNA sequence corresponding to the 16S rRNA sequence of Bacterium SOS2 is provided in SEQ ID No: 2 and the cDNA sequence corresponding to the 16S rRNA sequence of Bacterium SOS3 is provided in SEQ ID No: 3.

```
                                           SEQ ID No: 1
Bacterium SOS1
AAGTCGGACGGCAGCGCGGGGGCAACCCTGGCGGCGAGTGGCGAACGGGT

GAGTAATACATCGGAACGTGTCCTGGAGTGGGGGATAGCCGGCGAAAGCC

GGATTAATACCGATACGCTCTGTGGAGGAAAGCGGGGGATCTTCGGACCT

CGCGCTCAAGGGGCGGCCGATGGCAGATTAGCTAGTTGGTGGGGTAAAGG

CCTACCAAGGCGACGATCTGTAGCTGGTCTGAGAGGACGACCAGCCACAC

TGGGACTGAGACACGGCCCAGACTCCTACGGGAGGCAGCAGTGGGGAATT
```

-continued
TTGGACAATGGGGGCAACCCTGATCCAGCAATGCCGCGTGTGTGAAGAAG
GCCTTCGGGTTGTAAAGCACTTTTGTCCGGAAAGAAAACCGCTTCTCTAA
TACAGGGGCGGGATGACGGTACCGGAAGAATAAGCACCGGCTAACTACGT
GCCAGCAGCCGCGGTAATACGTAGGGTGCAAGCGTTAATCGGAATTACTG
GGCGTAAAGCGTGCGCAGGCGGTTCGCTAAGACCGATGTGAAATCCCCGG
GCTTAACCTGGGAACTGCATTGGTGACTGGCGGGCTAGAGTATGGCAGAG
GGGGGTAGAATTCCACGTGTAGCAGTGAAATGCGTAGAGATGTGGAGGAA
TACCGATGGCGAAGGCAGCCCCCTGGGCCAATACTGACGCTCATGCACGA
AAGCGTGGGGAGCAAACAGGATTAGATACCCTGGTAGTCCACGCCCTAAA
CGATGTCAACTAGTTGTCGGGTCTTCATTGACTTGGTAACGAAGCTAACG
CGTGAAGTTGACCGCCTGGGGAGTACGGTCGCAAGATTAAAACTCAAAGG
AATTGACGGGGACCCGCACAAGCGTGGATGATGTGGATTAATTCGATGCA
ACGCGAAAAACCTTACCTACCCTTGACATGTACGGAACCTTGCTGAGAGG
TGAGGGTGCCCGAAAGGGAGCCGTAACACAGGTGCTGCATGGCTGTCGTC
AGCTCGTGTCGTGAGATGTTGGGTTAAGTCCCGCAACGAGCGCAACCCTT
GTCCCTAGTTCGTACGCAAGAGCACTCTAGGGAGACTGCCGGTGACAAAC
CGGAGGAAGGTGGGGATGACGTCAAGTCCTCATGGCCCTTATGGGTAGGG
CTTCACACGTCATACAATGGTCGGAACAGAGGGTTGCNAAGCCGCGAGGT
GGAGCCAATCCCAGAAACCGATCGTAGTCCGGATCGCAGTCTGCAACTC
GACTGCGTGAAGCTGGAATCGCTAGTAATCGCGGATCAGCATGCCGCGGT
GAATACGTTCCCGGGTCTTGTACACACCGCCCGTCACACCATGGGAGTGG
GTTTTACCAGAAGTGGCTAGTCTAACCGCAAG SEQ ID No: 2
Bacterium SOS2
GCTGGCGGCATGCTTTACACATGCAAGTCGAACGGCAGCACGGGGCAAC
CCTGGTGGCGAGTGGCGAACGGGTGAGTAATACATCGGAACGTGTCCTGG
AGTGGGGGATAGCCCGGCGAAAGCCGGATTAATACCGCATACGCTCGGGA
GAGGAAAGCGGGGGACCTTCGGGCCTCGCGCTCAAGGGGCGGCCGATGGC
GGATTAGCTAGTTGGTGGGGTAAAGGCCTACCAAGGCGACGATCCGTAGC
TGGTCTGAGAGGACGACCAGCCACACTGGGACTGAGACACGGCCCAGACT
CCTACGGGAGGCAGCAGTGGGGAATTTTGGACAATGGGGGCAACCCTGAT
CCAGCAATGCCGCGTGTGCGAAGAAGGCCTTCGGTTGTAAAGCACTTTT
GTCCGGAAAGAAATCCTGCCTGATAATACCGGGCGGGATGACGGTACCG
GAAGAATAAGCACCGGCTAACTACGTGCCAGCAGCCGCGGTAATACGTAG
GGTGCGAGCGTTAATCGGAATTACTGGGCGTAAAGCGTGCGCAGGCGGTT
CGCTAAGACCGATGTGAAATCCCCGGGCTTAACCTGGGAACTGCATTGGT
GACTGGCGGGCTAGAGTATGGCAGAGGGGGTAGAATTCCACGTGTAGCA
GTGAAATGCGTAGAGATGTGGAGGAATACCGATGGCGAAGGCAGCCCCCT
GGGCCAATACTGACGCTCATGCACGAAAGCGTGGGGAGCAAACAGGATTA
GATACCCTGGTAGTCCACGCCCTAAACGATGTCAACTAGTTGTTGGGGAT
TCATTTCCTTAGTAACGAAGCTAACGCGTGAAGTTGACCGCCTGGGGAGT
ACGGTCGCAAGATTAAAACTCAAAGGAATTGACGGGGACCCGCACAAGCG
GTGGATGATGTGGATTAATTCGATGCAACGCGAAAAACCTTACCTACCCT
TGACATGGACGGAATCCCGCTGAGAGGTGGGAGTGCTCGAAAGAGAACCG
TCGCACAGGTGCTGCATGGCTGTCGTCAGCTCGTGTCGTGAGATGTTGGG
TTAAGTCCCGCAACGAGCGCAACCCTTGTCCTTAGTTGCTACGCAAGAGC
ACTCTAAGGAGACTGCCGGTGACAAACCGGAGGAAGGTGGGGATGACGTC
AAGTCCTCATGGCCCTTATGGGTAGGGCTTCACACGTCATACAATGGTCG
GAACAGAGGGTCGCCAACCCGCGAGGGGGAGCCAATCCCAGAAACCGAT
CGTAGTCCGGATTGCACTCTGCAACTCGAGTGCATGAAGCTGGAATCGCT
AGTAATCGCGGATCAGCATGCCGCGGTGAATACGTTCCCGGGTCTTGTAC
ACACCGCCCGTCACACCATGGGAGTGGGTTTTACCAGAAGTGGCTAGTCT
AACCGCAAGGAGGACGGTCACCACGGTAGGATTCATGACT SEQ ID No: 3
Bacterium SOS3
AGTGGGGGATAGCCCGGCGAAAGCCGGATTAATACCGCATACGATCTGAG
GATGAAAGCGGGGGACCGCAAGGCCTCGCGCTCAAGGAGCGGCCGATGGC
GGATTAGCTAGTTGGTGGGGTAAAGGCCCACCAAGGCGACGATCCGTAGC
TGGTCTGAGAGGACGACCAGCCACACTGGGACTGAGACACGGCCCAGACT
CCTACGGGAGGCAGCAGTGGGGAATTTTGGACAATGGGGCAACCCTGAT
CCAGCAATGCCGCGTGTGTGAAGAAGGCCTTCGGGTTGTAAAGCACTTTT
GTCCGGAAAGAAAACTTCGTCCCTAATATGGATGGAGGATGACGGTACCG
GAAGAATAAGCACCGGCTAACTACGTGCCAGCAGCCGCGGTAATACGTAG
GGTGCGAGCGTTAATCGGAATTACTGGGCGTAAAGCGTGCGCAGGCGGTG
ATGTAAGACCGATGTGAAATCCCCGGGCTTAACCTGGGAACTGCATTGGT
GACTGCATTGCTGGAGTATGGCAGAGGGGGTGGAATTCCACGTGTAGCA
GTGAAATGCGTAGAGATGTGGAGGAACACCGATGGCGAAGGCAGCCCCCT
GGGCCAATACTGACGCTCATGCACGAAAGCGTGGGGAGCAAACAGGATTA
GATACCCTGGTAGTCCACGCCCTAAACGATGTCAACTGGTTGTCGGGCCT
TCATTGGCTTGGTAACGTAGCTAACGCGTGAAGTTGACCGCCTGGGGAGT
ACGGTCGCAAGATTAAAACTCAAAGGAATTGACGGGGACCCGCACAAGCG
GTGGATGATGTGGATTAATTCGATGCAACGCGAAAAACCTTACCTACCCT
TGACATGGACGGAACCTCGATGAGAGTTGAGGGTGCCCGAAAGGGAGCCG
TCACACAGGTGCTGCATGGCTGTCGTCAGCTCGTGTCGTGAGATGTTGGG
TTAAGTCCCGCAACGAGCGCAACCCTTGTCCCTGGTTGCTACGCAAGAGC
ACTCCAGGGAGACTGCCGGTGACAAACCGGAGGAAGGTGGGGATGACGTC
AAGTCCTCATGGCCCTTATGGGTAGGGCTTCACACGTCATACAATGGTCG
GAACAGAGGGTTGCCAAGCCGCGAGGTGGAGCCAATCCCAGAAACCGAT
CGTAGTCCGGATCGCAGTCTGCAACTCGACTGCGTGAAGCTGGAATCGCT
AGTAATCGCGGATCAGCATGCCGCGGTGAATACGTTCCCGGGTCTTGTAC
ACACCGCCCGTCACACCATGGGAGTGGGTTTTACCAGA Maintenance of Culture.

The strains are stored as a 30% glycerol stock at −80° C. For short-term storage the strain is maintained on R2A-agar plates. The cultures are routinely grown at 28° C. for 2 days and the freshly grown colonies on the plate are kept at 4° C. with subculturing every 4 weeks.

Example 2—Isolation of Plant-Beneficial *Burkholderia*-Like Species

Figure 2:
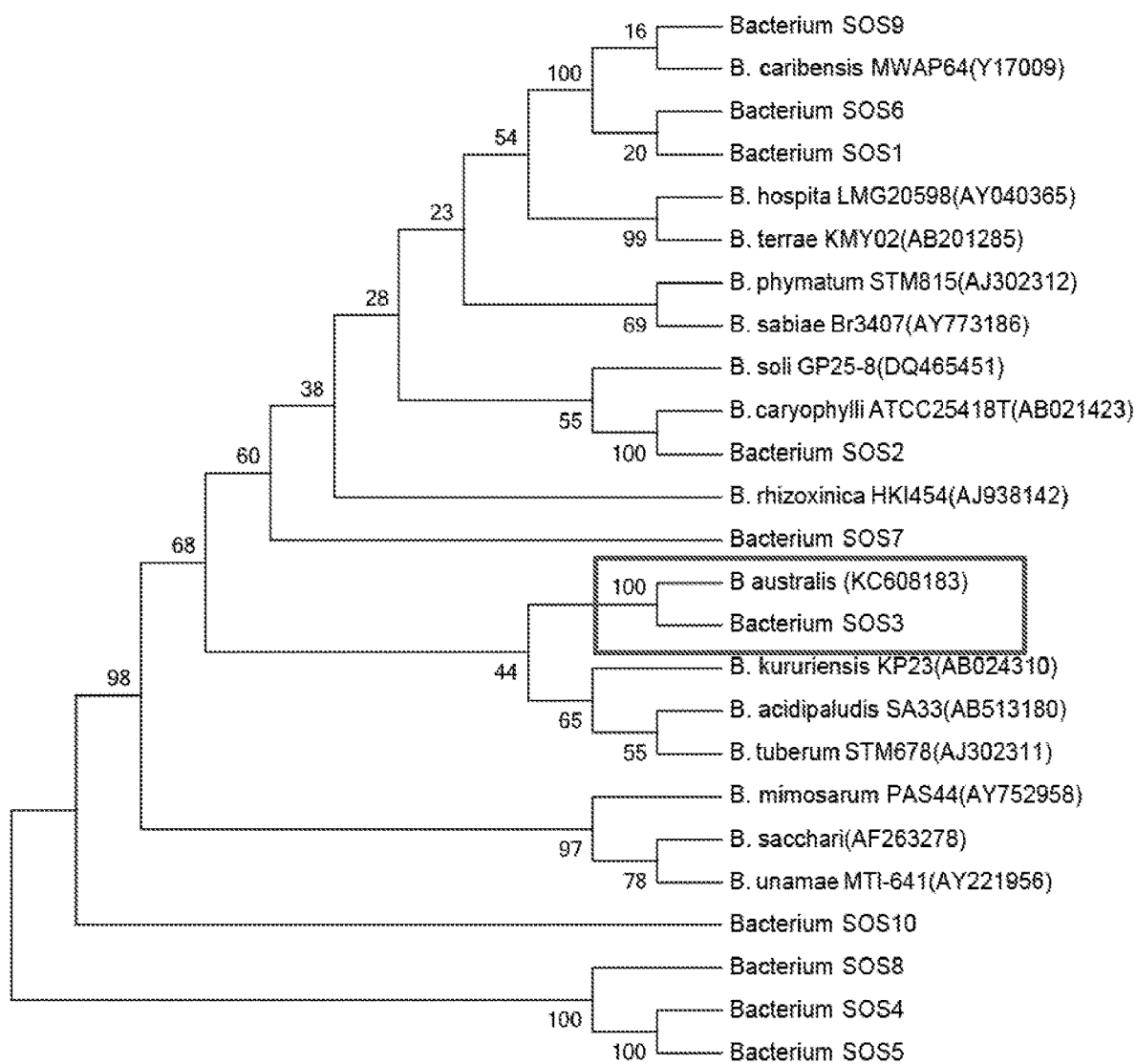
FIG. 2 illustrates a phylogenetic tree with 10 bacterial clones isolated from the tomato rhizosphere and identified as *Burkholderia* using 16S rRNA primers OTU11burkhold_R: GTTGGCAACCCTCTGTTC) and 926F: AAACTYAAAK-GAATTGACGG.

*Burkholderia australis* Q208 related strains (BARS) were isolated as follows: 10 g of pooled roots of sugar cane or rice (for *Burkholderia australis* Q208) or 10 g of pooled roots of tomato (for Bacterium SOS1, Bacterium SOS2 and Bacterium SOS3) were homogenised in a vegetable juicer (Breville) with 10 ml sterile phosphate-buffered saline, pH 7.2 for 1 min at high speed. The homogenized sample was filtered through Whatman paper number 1, and serial dilutions (up to $10^{-9}$) were made with the filtrate. 100 µl of each dilution was spread on agar plates containing R2A minimal medium and, in the case of BRS, phytate at a concentration of 4 g/L. Plates were incubated at 28° C. for 5 days. The plates containing separated individual bacterial colonies were used for PCR screening. For identification of BRS 16S rRNA specific primers for *Burkholderia* OTU11burkhold_R: GTTGGCAACCCTCTGTTC and 926F: AAACTYAAAKGAATTGACGG were applied. Using this method 10 independent colonies were isolated which had 96%-100% 16S rRNA sequence identity to *Burkholderia* sp. Q208 (FIG. 2). After laboratory and plant growth experiments three species showed the best plant growth-promotion results: Bacterium SOS1 (96% sequence identity to *Burkholderia* sp. Q208), Bacterium SOS2 (98% sequence identity to *Burkholderia* sp. Q208) and Bacterium SOS3 (100% sequence identity to *Burkholderia* sp. Q208) (FIG. 2). All three bacteria (Bacteria SOS1-SOS3) are able to fix nitrogen, solubilize phytate, and form biofilm on the plant roots.

Example 3—Treatment of Seeds and Plantlets with Plant-Beneficial *Burkholderia*-Like Species Seeds of tomato, rice, or lettuce were soaked into the solution containing BARS at the concentration of $1 \times 10^9$ cell per ml for 15 minutes. Control seeds were soaked in pure water for 15 mins prior to planting. Three replicas of each treatment group, including control, were used. The seeds or seedlings were planted according to the established methods used for hydroponic, greenhouse or field trials.

Example 4—Composition of the Hydroponic and Greenhouse Fertilisers

Composition of the Organic Phytate Biofertiliser ("Phytoliser").
The biofertiliser for hydroponic and greenhouse applications ("phytoliser") is a two-component system. It comprises of BARS at final concentration of $1 \times 10^9$ cell per ml, and of the organic matter described below, as liquid solution. The bacterial strains were grown and maintained as described in Example 1, and delivered to the trial spot as lyophilised powder. At the trial spot the bacteria were transferred to 100 ml of pure water (making $1 \times 10^6$ concentration) and left for 1 hr for their recovery. The organic matter (phytate) containing necessary chemical elements is manufactured from the plants, or from pig or chicken manure. The major component of the phytoliser is phytate, which represents the organic phosphorus stored by plants and abundantly found in different kinds of manures, plants and seeds. The phytoliser also contains a number of other chemical elements in the form of organic molecules, which are necessary for plant growth. Thus, all the inorganic nutrients in the recipe are substituted with organic nutrients, where the necessary chemical elements represent the parts of the organic molecules. Concentration of the chemical elements in the biofertiliser corresponds to the average concentration used for hydroponic applications in current practices, as shown in Table 1.

TABLE 1

Concentration of chemical elements in the phytoliser.

| Nutrient | Delivered nutrient concentration (ppm)[z] | |
|---|---|---|
| | Minimal | Maximum |
| N | 0 | 70 |
| P | 50 | 150 |
| K | 120 | 200 |
| Ca | 100 | 200 |
| Mg | 30 | 60 |
| S | 30 | 60 |
| Fe | 2.0 | 3.0 |
| Cu | 0.1 | 0.3 |
| Mn | 0.5 | 1.0 |
| Zn | 0.2 | 0.5 |
| B | 0.5 | 1.0 |
| Mo | 0.05 | 0.1 |

1 ppm = 1 mg/liter

Figure 3:
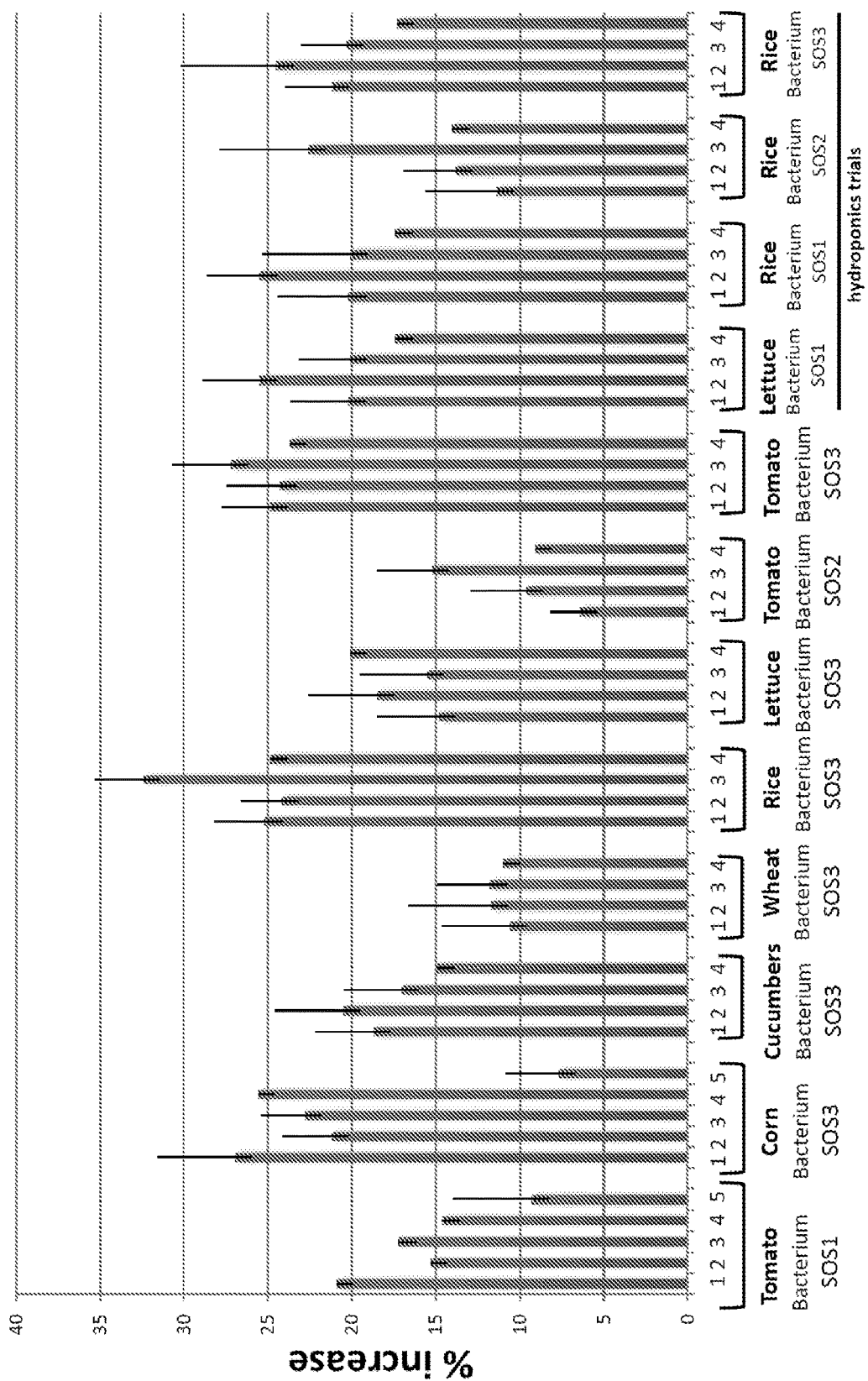
FIG. 3 illustrates the effect of plant-growth-promoting bacteria on plant growth and seed germination.

Composition of the Partially Organic Phytate Fertiliser.
In separate trials, highly purified phytate (98% purity) was mixed with the other 10 chemical elements (see Table 1) necessary for plant growth (K, Ca, Mg, S, Fe, Cu, Mn, Zn, B, and Mo). The roots of rice plantlets were soaked in a solution containing BARS and then left growing in the medium containing crude phytate solution. The plantlets grew faster than the control plants incubated with a standard hydroponic medium and their roots appeared thicker (FIG. 3). In FIG. 3, bars indicate % of increase compared to non-inoculated plants. Error bars are SE from 10 replicas per same treatment. 1-root length; 2-root dry mass; 3-shoot length; 4-shoot dry mass; 5-seed germination. The trials were conducted whether in soil or hydroponic conditions. This fertiliser provides the opportunity to enhance plant growth, however, those conditions potentially may not be considered as fully "organic". This recipe also allows avoiding the usage of the mineral phosphate and nitrogen-based fertilisers, thus minimizing concentration of nitrates in the final product.

Example 5—Composition and Preparation of Biofertilisers for Field Applications Preparation of Biofertilizer.
BARS are mixed thoroughly with Alginate-humic acid mixture. This suspension was capsulated in the presence of solution of $CaCl_2$, converting water-soluble sodium alginate into the water-insoluble calcium alginate beads. The beads are then coated with a mixture of phytate and manure, and air dried. Such biofertilizer pellets can be stored for months at room temperature. When pellets are applied to the wet soil, the bacteria start reviving and proliferating. Then, by direct contact with the roots the bacteria form biofilm on the roots, providing nutrients to the plants.
A further exemplary method for producing the biofertiliser is as follows. Alginate beads were prepared according to the methods outlined in Young et al. (Young C C, Rekha P D, Lai W A, Arun A B. Encapsulation of plant growth-promoting bacteria in alginate beads enriched with humic acid. Biotechnol Bioeng. 2006 Sep. 5; 95(1):76-83). A mixture of 2.5 ml of 10% humic acid and 750 ml of 30% glycerol were added to 2% sodium alginate solution to obtain a final volume of 25 ml. The bacterial culture (250 ml) was centrifuged, the cell pellet was washed with saline (0.85% NaCl, w/v) and suspended in 25 ml of alginate-humic acid mixture and mixed thoroughly. This suspension was extruded through a 26-gauze needle drop wise into a pre-cooled sterile 1.5% (w/v) aqueous solution of $CaCl_2$ under mild agitation. The water-soluble sodium alginate was converted into water-insoluble calcium alginate beads. Thus instantaneously formed beads were allowed to harden for 3-6 h at room temperature. Beads were collected by sieving and were washed several times with sterile water.

Example 6—Tomato, Rice and Lettuce Trials

Hydroponic and Greenhouse Trials.

The phytoliser compositions are described in Example 4. The seedlings or plantlets of tomato, rice and lettuce were treated with BARS as described in Example 3 before planting. Non-treated plants were used as a control. Other controls included: for hydroponic trials, water only, and commercially available inorganic fertilisers; for greenhouse trials, water only and the commercially available fertiliser FlowPhos (Yara Nipro). In all experiments the experimental plants grew faster than the control plants (FIG. 3) and dry mass of plants grown with addition of BRS was significantly higher (up to 30%) than that of the control plants.

Field Trials.

Tomato seeds and plantlets were used for field trials. They were used either treated as in Example 3 or untreated. The fields were prepared as follow: cow, chicken, or pig manure, or different combinations of these manures is mixed with soil (upper 20-50 cm layer) in a range of concentration varying from 0.1 to 1% w/w, in order to provide adequate concentration of the organic nutrients, including phytate. Then biofertilizer pellets (Example 5) are applied to the soil (upper 20-50 cm layer) in a concentration range varying between 0.01 to 0.1% w/w. The pellets allow retaining bacteria in the soil for a long period of time, keeping their concentration relatively high, compared to other microorganisms. This soil is used for planting of the bacteria-treated and untreated seeds or plantlets (Example 3). For those trials controls were untreated seeds and plantlets with commercial inorganic fertiliser used in conventional practice, and untreated seeds and plantlets with pure organic fertilisers. The results of the field trials (FIG. 3) were similar to those obtained in the glasshouse conditions with average dry mass increase of 10-30%.

Example 6. Seed Germination Enhancement

Tomato and corn seeds were coated with Bacterium SOS' or Bacterium SOS3 in a solution of CMC (4% w/v). The control seeds were treated with CMC (4% w/v) only. After placing the seeds in the soil conditions the number of appeared plants were counted and significant improvement of the germination rate was detected (FIG. 3).

Hydroponics Trials:

Pre-germination of lettuce or rice seeds was conducted for 4 to 5 days in trays lined with damp paper and covered with plastic. When the roots reached 1-2 cm in length the seedlings were dipped in a solution containing bacteria in the concentration of 107 cells/ml and relocated into small pots with vermiculite. Growth solution was supplied via capillary action from below. The measurements of the plant roots and shoots were conducted after 4 weeks post transplantation. The hydroponic medium contained 0.1% phytate solution (50% phytate purity, Lvyu Chemical Co., Ltd or Henan Kingway Chemicals Co., Ltd.).

REFERENCES 1. http://www.fao.org/statistics/en/
2. Bhattacharyya P N, Jha D K. Plant growth-promoting rhizobacteria (PGPR): emergence in agriculture. World J Microbiol Biotechnol. 2012 April; 28(4):1327-50. doi: 10.1007/s11274-011-0979-9. Epub 2011 Dec. 24. Review. PubMed PMID: 22805914.
3. Miransari M. Soil microbes and plant fertilization. Appl Microbiol Biotechnol. 2011 December; 92(5):875-85. doi: 10.1007/s00253-011-3521-y. Epub 2011 Oct. 12. Review. PubMed PMID: 21989562.
4. http://news.monsanto.com/press-release/corporate/monsanto-and-novozymes-team-provide-sustainable-bioagricultural-solutions
5. Mulvaney R L, Khan S A, Ellsworth T R. Synthetic nitrogen fertilizers deplete soil nitrogen: a global dilemma for sustainable cereal production. J Environ Qual. 2009 Oct. 29; 38(6):2295-314. doi: 10.2134/jeq2008.0527. Print 2009 November-December Review. PubMed PMID: 19875786.
6. Sharma S B, Sayyed R Z, Trivedi M H, Gobi T A. Phosphate solubilizing microbes: sustainable approach for managing phosphorus deficiency in agricultural soils. Springerplus. 2013 Oct. 31; 2:587. doi: 10.1186/2193-1801-2-587. eCollection 2013. Review. PubMed PMID: 25674415; PubMed Central PMCID: PMC4320215.
7. Carroll P. Vance, Claudia Uhde-Stone, Deborah L. Allan. Phosphorus acquisition and use: critical adaptations by plants for securing a nonrenewable resource. New Phytologist. (2003) DOI: 10.1046/j 0.1469-8137.2003.00695.x
8. Choudhury A T, Kennedy I R, Ahmed M E, Kecskés M L. Phosphorus fertilization for rice and control of environmental pollution problems. Pak J Biol Sci. 2007 Jul. 1; 10(13):2098-105. Review. PubMed PMID: 19070168.
9. Naik P R, Raman G, Narayanan K B, Sakthivel N. Assessment of genetic and functional diversity of phosphate solubilizing fluorescent pseudomonads isolated from rhizospheric soil. BMC Microbiol. 2008 Dec. 20; 8:230. doi:10.1186/1471-2180-8-230. PubMed PMID: 19099598; PubMed Central PMCID: PMC2625360.
10. Paunngfoo-Lonhienne C, Lonhienne T G A, Yeoh Y K, Webb R I, Laksmanan P, Chan C X, Lim P-E, Ragan M A, Schmidt S and Hugenholtz P. A new species of *Burkholderia* isolated from sugarcane roots promotes plant growth. Microbial Biotechnology 2014 7(2): 142.

The invention claimed is:

1. A method of increasing plant growth, plant productivity, seed germination or soil quality for: (i) a dicotyledonous plant, or (ii) a monocotyledonous plant selected from wheat, rice, and corn; the method comprising the step of: applying to the plant a treatment agent comprising at least one plant-beneficial *Burkholderia*-like species, wherein the at least one plant-beneficial *Burkholderia*-like species has at least 99% 16S rRNA sequence identity to Bacterium SOS3 in SEQ ID No: 3 (deposited on 2 Jun. 2016 under Accession No. V16/013910 at the National Measurement Institute, 1/153 Bertie Street Port Melbourne, Victoria, Australia 3207), and wherein the at least one plant-beneficial *Burkholderia*-like species is configured to form biofilms on the roots of the plant and wherein the at least one plant-beneficial *Burkholderia*-like species is not *Burkholderia* strain Q208.

2. The method of claim 1, wherein the method is a method of promoting plant growth;
wherein the step of applying to the plant the treatment agent is a step of treating seeds or seedlings of the dicotyledonous plant, or the monocotyledonous plant with an effective amount of the treatment agent, wherein the at least one plant-beneficial *Burkholderia*-like species is configured to form biofilms on the roots of the seedlings or seedlings grown from the seeds;
wherein the method further comprises the steps of:
growing the seeds or seedlings in a soil-free growth medium for an initial time period to grow into plantlets; and
transferring the plantlets to field or greenhouse conditions.

3. The method of claim 2, wherein at least a part of the soil-free growth medium comprises the treatment agent.

4. The method of claim 2, wherein the plantlets when transferred are cultivated in soil comprising fertiliser or manure treated with an additional amount of the treatment agent.

5. The method of claim 2, wherein the step of treating the seeds or seedlings comprises co-treatment with at least one of the group consisting of: a phospholipid, a phosphoprotein, a phosphoester, a sugar phosphate and a phytate.

6. The method of claim 2, wherein the at least one plant-beneficial *Burkholderia*-like species is Bacterium SOS3 (deposited on 2 Jun. 2016 under Accession No. V16/013910 at the National Measurement Institute, 1/153 Bertie Street Port Melbourne, Victoria, Australia 3207).

7. The method of claim 1, wherein the treatment agent is a fertiliser composition comprising the at least one plant-beneficial *Burkholderia*-like species.

8. The method of claim 7, wherein the at least one plant-beneficial *Burkholderia*-like species is Bacterium SOS3 (deposited on 2 Jun. 2016 under Accession No. V16/013910 at the National Measurement Institute, 1/153 Bertie Street Port Melbourne, Victoria, Australia 3207).

9. The method of claim 7, wherein the fertiliser composition further comprises at least one plant nutrient.

10. The method of claim 9, wherein the at least one plant nutrient comprises manure or compost.

11. The method of claim 9, wherein the at least one plant nutrient comprises one or more of the group consisting of: a phospholipid, a phosphoprotein, a phosphoester, a sugar phosphate and a phytate.

12. The method of claim 1, wherein the method is a method of growing seedlings, wherein the step of applying to the plant the treatment agent is a step of growing seedlings of the dicotyledonous plant, or the monocotyledonous plant in a soil-free growth medium comprising the at least one plant-beneficial *Burkholderia*-like species.

13. The method of claim 12, wherein the at least one plant-beneficial *Burkholderia*-like species is Bacterium SOS3 (deposited on 2 Jun. 2016 under Accession No. V16/013910 at the National Measurement Institute, 1/153 Bertie Street Port Melbourne, Victoria, Australia 3207).

14. The method of claim 12, wherein the soil-free growth medium further comprises at least one plant nutrient.

15. The method of claim 14, wherein the at least one plant nutrient comprises one or more of the group consisting of: a phospholipid, a phosphoprotein, a phosphoester, a sugar phosphate and a phytate.

16. The method of claim 1, wherein the at least one plant-beneficial *Burkholderia*-like species has 100% sequence identity to Bacterium SOS3 in SEQ ID No. 3.

* * * * *